United States Patent
Lamanna et al.

(10) Patent No.: US 9,562,212 B2
(45) Date of Patent: Feb. 7, 2017

(54) SURFACTANTS AND METHODS OF MAKING AND USING SAME

(71) Applicant: 3M INNOVATIVE PROPERTIES COMPANY, St. Paul, MN (US)

(72) Inventors: William M Lamanna, Stillwater, MN (US); Patricia M. Savu, Maplewood, MN (US); Jason M Kehren, Stillwater, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/262,678

(22) Filed: Sep. 12, 2016

(65) Prior Publication Data

US 2016/0376533 A1 Dec. 29, 2016

Related U.S. Application Data

(63) Continuation of application No. 14/763,841, filed as application No. PCT/US2014/010769 on Jan. 9, 2014, now Pat. No. 9,454,082.

(60) Provisional application No. 61/757,790, filed on Jan. 29, 2013.

(51) Int. Cl.
    *G03F 7/40* (2006.01)
    *C11D 7/32* (2006.01)
    *C11D 11/00* (2006.01)
    *C11D 1/00* (2006.01)
    *G03F 7/42* (2006.01)
    *C08F 290/06* (2006.01)
    *C07C 311/00* (2006.01)
    *C07C 303/36* (2006.01)
    *C08F 14/18* (2006.01)

(52) U.S. Cl.
    CPC ......... *C11D 11/0047* (2013.01); *C07C 303/36* (2013.01); *C07C 311/00* (2013.01); *C08F 14/18* (2013.01); *C08F 290/062* (2013.01); *C08F 290/065* (2013.01); *C11D 1/004* (2013.01); *G03F 7/40* (2013.01); *G03F 7/426* (2013.01)

(58) Field of Classification Search
    CPC ..... G03F 7/40; C08F 290/062; C08F 290/065; C07C 303/36; C07C 311/00
    USPC ...... 510/176; 134/1.3; 430/331; 558/413, 48
    See application file for complete search history.

(56) References Cited

U.S. PATENT DOCUMENTS

| | | |
|---|---|---|
| 3,734,962 A | 5/1973 | Niederprum |
| 4,089,804 A | 5/1978 | Falk |
| 5,043,195 A | 8/1991 | Skrivseth |
| 5,688,884 A | 11/1997 | Baker |
| 6,852,781 B2 | 2/2005 | Savu |
| 7,169,323 B2 | 1/2007 | Parent |
| 7,572,848 B2 | 8/2009 | Savu |
| 7,741,260 B2 | 6/2010 | Koshiyama |
| 2008/0280230 A1 | 11/2008 | Chang |
| 2008/0299485 A1 | 12/2008 | Savu |
| 2008/0299487 A1 | 12/2008 | Chang |
| 2010/0160458 A1 | 6/2010 | Savu |

FOREIGN PATENT DOCUMENTS

WO WO 2013-022673 2/2013

OTHER PUBLICATIONS

Huang, "Effect of Novel rinsing material and surfactant treatment on the resist pattern performance", Proceedings of SPIE, 2007, vol. 6519, pp. 65193C-1-65193C-9.
Miyahara, "Improvement of pattern collapse issue by additive added D.I water rinse process 2", Proceedings of SPIE, 2004, vol. 5376, pp. 830-841.
Spyridon Advances in Resist Technology and Processing XXI, J.L. Sturtevant, Ed., Proc. of SPIE, vol. 5376 (2004).
Tanaka, "Improvement of pattern collapse issue by additive added D.I water rinse process", Proceedings of SPIE, 2003, vol. 5039, pp. 1366-1381.
International Search Report for PCT International Application No. PCT/US2014/010769 mailed on Apr. 29, 2014, 2 pages.

*Primary Examiner* — Amanda C Walke
(74) *Attorney, Agent, or Firm* — Adam Bramwell

(57) ABSTRACT

Anionic surfactants have a formula:
$R_fSO_2N(H)$—$CH_2CH(CH_3)OH$; or
$R_fSO_2N(H)$—$(CH_2CH_2O)_xH$, where x is an integer from 2-6. $R_f$ is a fluoroalkyl group having 3 to 8 carbon atoms. Neutral surfactants having a formula:
(a) $R_fSO_2N[CH_2CH(CH_3)OH]_2$;
(b) $R_fSO_2N[CH_2CH(CH_3)OH][(CH_2CH_2O)_nH]$, where n is an integer from 1-6;
(c) $R_fSO_2N(R)[(CH_2CH_2O)_pH]$, where p is an integer from 2-6, and R is an alkyl group having 1 to 4 carbon atoms; or
(d) $R_fSO_2N[(CH_2CH_2O)_qH][(CH_2CH_2O)_mH]$, where q is an integer from 1-6 and m is an integer from 3-6. $R_f$ is a fluoroalkyl group having 3 to 8 carbon atoms.

11 Claims, No Drawings

SURFACTANTS AND METHODS OF MAKING AND USING SAME

CROSS REFERENCE TO RELATED APPLICATIONS

This application is a continuation of U.S. application Ser. No. 14/763,841, filed Jul. 28, 2015, issued as U.S. Pat. No. 9,454,082, which was a national stage filing under 35 U.S.C. 371 of PCT/US2014/010769, filed Jan. 9, 2014, which claims priority to U.S. Provisional Application No. 61/757,790 filed Jan. 29, 2013, the disclosure of which is incorporated by reference in its/their entirety herein.

FIELD

The present disclosure relates to fluorinated surfactants, and methods of making and using the same.

BACKGROUND

Various fluorinated surfactants are described, for example, in U.S. Pat. Nos. 4,089,804 and 7,741,260, U.S. Patent Application Pub. Nos. 2008/0299487 and 2008/0280230, and V. Huang et al., *Proc. of SPIE*, Vol. 6519, 65193C-1 (2007).

SUMMARY

In some embodiments, anionic surfactants are provided. The anionic surfactants have a formula:
$R_fSO_2N(H)$—$CH_2CH(CH_3)OH$; or
$R_fSO_2N(H)$—$(CH_2CH_2O)_xH$, where x is an integer from 2-6. $R_f$ is a fluoroalkyl group having 3 to 8 carbon atoms.

In some embodiments, neutral surfactants are provided. The neutral surfactants have a formula:
(a) $R_fSO_2N[CH_2CH(CH_3)OH]_2$;
(b) $R_fSO_2N[CH_2CH(CH_3)OH][(CH_2CH_2O)_nH]$, where n is an integer from 1-6;
(c) $R_fSO_2N(R)[(CH_2CH_2O)_pH]$, where p is an integer from 2-6, and R is an alkyl group having 1 to 4 carbon atoms; or
(d) $R_fSO_2N[(CH_2CH_2O)_qH][(CH_2CH_2O)_mH]$, where q is an integer from 1-6 and m is an integer from 3-6. $R_f$ is a fluoroalkyl group having 3 to 8 carbon atoms.

In some embodiments, fluorinated sulfonamide surfactant compositions are provided. The compositions include an anionic surfactant according to the formula:
$R_fSO_2N(H)$—$CH_2CH(CH_3)OH$; or
$R_fSO_2N(H)$—$(CH_2CH_2O)_xH$, where x is an integer from 2-6; or
a neutral surfactant according to the formula:
$R_fSO_2N[CH_2CH(CH_3)OH]_2$;
$R_fSO_2N[CH_2CH(CH_3)OH][(CH_2CH_2O)_nH]$, where n is an integer from 1-6;
$R_fSO_2N(R)[(CH_2CH_2O)_pH]$, where p is an integer from 2-6, and R is an alkyl group having 1 to 4 carbon atoms; or
$R_fSO_2N[(CH_2CH_2O)_qH][(CH_2CH_2O)_mH]$, where q is an integer from 1-6, m is an integer from 1-6, and (q+m)≥3; and
a solvent. $R_f$ is a fluoroalkyl group having 3 to 8 carbon atoms.

In some embodiments, fluorinated sulfonamide surfactant compositions are provided. The compositions include an anionic surfactant according to the formula:
$R_fSO_2N(H)$—$CH_2CH(CH_3)OH$;
$R_fSO_2N(H)$—$(CH_2CH_2O)_xH$, where x is an integer from 2-6; or
$R_fSO_2N(H)$—$CH_2CH_2OH$; and
a neutral surfactant according to the formula:
$R_fSO_2N[CH_2CH(CH_3)OH]_2$;
$R_fSO_2N[CH_2CH(CH_3)OH][(CH_2CH_2O)_nH]$, where n is an integer from 1-6;
$R_fSO_2N(R)[(CH_2CH_2O)_pH]$, where p is an integer from 2-6 and R is an alkyl group having 1 to 4 carbon atoms;
$R_fSO_2N[(CH_2CH_2O)_qH][(CH_2CH_2O)_mH]$, where q is an integer from 1-6, m is an integer from 1-6, and q+m≥3; or
$R_fSO_2N[CH_2CH_2OH]_2$; and
a solvent. $R_f$ is a fluoroalkyl group having 3 to 8 carbon atoms. If the composition comprises appreciable amounts of only one anionic surfactant and only one neutral surfactant, and the anionic surfactant is $R_fSO_2N(H)$—$CH_2CH_2OH$, then the neutral surfactant is not $R_fSO_2N[CH_2CH_2H]_2$.

The above summary of the present disclosure is not intended to describe each embodiment of the present disclosure. The details of one or more embodiments of the disclosure are also set forth in the description below. Other features, objects, and advantages of the disclosure will be apparent from the description and from the claims.

DETAILED DESCRIPTION

The present disclosure describes fluorinated sulfonamide surfactants and surfactant compositions that may be particularly useful as surface active agents in aqueous solutions. The surfactants and compositions may provide a number of advantages relative to known surfactants, including, for example, improved water solubility, reduced surface tensions in aqueous media, controlled wetting, and controlled absorption onto or into photoresists. Applications for the surfactants and surfactant compositions of the present disclosure include, for example, use as wetting agents, cleaning surfactants, coating surfactants for improved leveling and reduced coating defects, and buffered oxide etch (BOE) surfactants. An additional application for the surfactants and surfactant compositions of the present disclosure is their use as photoresist developer rinse surfactants used in semiconductor processing as described in U.S. Pat. No. 7,741,260; U.S. Patent Application Pub. No. 2008/0280230; and in V. Huang et al., *Proc. of SPIE*, Vol. 6519, 65193C-1 (2007); S. Spyridon et al., Advances in Resist Technology and Processing XXI, J. L. Sturtevant Ed., *Proc. of SPIE*, Vol. 5376 (SPIE, Bellingham, W A, 2004); K. Tanaka et al., Advances in Resist Technology and Processing XX, T. Fedynyshyn, Ed., *Proc. of SPIE*, Vol. 5039 (2003); and O. Miyahara et al., Advances in Resist Technology and Processing XXI, J. L. Sturtevant Ed., *Proc. of SPIE*, Vol. 5376 (SPIE, Bellingham, W A, 2004).

In semiconductor processing, typically, an integrated circuit consisting of a series of patterned functional layers (insulators, metal wires, etc) is formed. The structure of each layer is transferred from a mask via photolithography followed by etching or ion implantation. In the photolithographic process, the functional layer is covered by a photoresist film. The circuits are typically fabricated with a chemically amplified photoresist consisting of a polymer with an acid-labile pendant protecting group, photoacid generator (PAG), and additional additives. Upon exposure to UV radiation through a patterned mask, the PAG is decomposed, generating a low concentration of acid. In the post-exposure bake step, the acid diffuses and catalyzes a deprotection reaction that cleaves the pendant group of the insoluble polymer resulting in a polymer that is soluble in the developer solution. The exposed positive tone photoresist is then removed, generally using solutions including tetramethyl ammonium hydroxide, leaving a pattern of unexposed photoresist lines, or features.

The semiconductor industry is rapidly migrating towards minimal feature size (e.g., less than 100 nm, less than 50 nm, less than 30 nm, or even less than 20 nm). To fulfill the demands for feature size reduction, critical dimensions of the photoresist structures must shrink adequately. Their heights cannot be reduced in the same way since etch resistance must be retained, forcing an increase in aspect ratio. With increasing aspect ratio, the mechanical strength of the photoresist lines decreases, leading to collapse of the structures during the development or post development processing. This pattern collapse is caused, at least in part, by unbalanced capillary forces acting between the lines after development and during the rinse and drying steps. It has been demonstrated that the surface tension of the rinse fluid and the contact angle of the rinse fluid on the photoresist are key parameters of the rinse fluid affecting pattern collapse. A promising approach to reduce pattern collapse is to incorporate surfactant solutions in the development and/or post-development rinse steps of the photolithographic process. To date, surfactant solutions have exhibited performance limitations when employed on very small feature sizes (e.g., less than about 28 nm). These deficiencies generally relate to the cleaning performance of the surfactant and its impact on the melting of resist features and defectivity (water mark and particle defects). Consequently, improved surfactant formulations that provide better performance for next generation high resolution wafer processing (e.g., feature sizes of less than 28 nm, less than 22 nm, less than 20 nm, less than 16 nm and beyond) in photoresist developer rinse applications may be desirable.

Definitions

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g. 1 to 5 includes 1, 1.5, 2, 2.75, 3, 3.8, 4, and 5).

As used herein, the phrase "anionic surfactants" refers to fluorinated sulfonamide surfactants having acidic hydrogens that are readily deprotonated in the presence of a weak or strong base to form an anion salt of the conjugate acid. In their deprotonated form, anionic surfactants can be paired with any cation including, for example, $NH_4^+$ and $Me_4N^+$, $Bu_4N^+$. The anionic surfactants of the present disclosure can exist in their neutral protic forms or as their anion salts or a mixture of neutral and anion salt forms in solution, depending on the pH of the solution.

As used herein, the phrase "neutral surfactants" refers to fluorinated sulfonamide surfactants having no strongly acidic hydrogens (i.e., pKa>10, preferably pKa>15) and, therefore, that do not readily react with weak or strong base in aqueous solution to form anionic species. The composition and state of charge of the neutral surfactants of the present disclosure may be essentially independent of pH.

As used herein, the phrase "mixed surfactant" or surfactant blends refer to compositions that include at least one anionic surfactant and at least one neutral surfactant.

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In some embodiments, the present disclosure describes fluorinated sulfonamide surfactants. The fluorinated sulfonamide surfactants may include an anionic surfactant having a structure as follows:

$R_fSO_2N(H)$—$CH_2CH(CH_3)OH$; or
$R_fSO_2N(H)$—$(CH_2CH_2O)_xH$, where x is an integer from 2-6, 2-5, 2-4, or 2-3. Alternatively, the fluorinated sulfonamide surfactants may include a neutral surfactant having a structure as follows:

$R_fSO_2N[CH_2CH(CH_3)OH]_2$;
$R_fSO_2N[CH_2CH(CH_3)OH][(CH_2CH_2O)_nH]$, where n is an integer from 1-6, 1-5, 1-4, or 1-3;
$R_fSO_2N(R)[(CH_2CH_2O)_pH]$, where p is an integer from 2-6, 2-5, 2-4, or 2-3, and R is an alkyl group having 1 to 4 carbon atoms; or
$R_fSO_2N[(CH_2CH_2O)_qH][(CH_2CH_2O)_mH]$, where q is an integer from 1-6, or 1-5, 1-4, or 1-3 and m is 3-6, 3-5, 3-4, or 3.

In some embodiments, to facilitate maximum solubility in water, at least one of the non-fluorinated groups bound to the sulfonamide nitrogen atom of either the anionic or neutral surfactant may be an oligomeric ethylene oxide group, wherein the oligomeric ethylene oxide group has 2-6, 2-5, 2-4, or 2-3 ethylene oxide repeat units.

In an alternative embodiment, the fluorinated sulfonamide surfactants may include anionic and neutral surfactants having a structure as follows:

$R_fSO_2N(H)$—$[CH_2CH(CH_3)O]_zH$, where z is an integer from 2-6, 2-5, 2-4, or 2-3; or
$R_fSO_2N[(CH_2CH(CH_3)O)_yH][(CH_2CH(CH_3)O)_jH]$;
where y is an integer from 1-6, 1-5, 1-4, 1-3; or 1-2; and j is an integer from 2-6, 2-5, 2-4, or 2-3; or
$R_fSO_2N[(CH_2CH(CH_3)O)_kH][(CH_2CH_2O)_nH]$, where n is an integer from 1-6, 1-5, 1-4, or 1-3; and k is an integer from 2-6, 2-5, 2-4, or 2-3.

Similar anionic and neutral fluorinated sulfonamide surfactant structures wherein the ethylene oxide and propylene oxide groups are co-oligomerized in the same chain, as exemplified in —$CH_2CH_2O$—$CH_2CHCH_3OH$ or —$CH_2CHCH_3O$—$CH_2CH_2OH$, are also possible. The fluorinated sulfonamide surfactants of the present disclosure may include such surfactants, including higher oligomers.

For the above-described fluorinated sulfonamide surfactants, each $R_f$ may independently be a fluoroalkyl group having 3 to 8 carbon atoms. The fluoroalkyl group may be straight chain, branched chain, or cyclic, and may be saturated or unsaturated. The fluoroalkyl group chain may be interrupted by catenary heteroatoms (e.g., O and N). The fluororoalkyl group may have any degree of fluorination. In various embodiments, $R_f$ may be a fluoroalkyl group having 4 to 6 carbon atoms. In further embodiments, $R_f$ may be a saturated perfluoroalkyl group having 4 to 6 carbon atoms. Still further, $R_f$ may be a saturated perfluoroalkyl group having 4 carbon atoms.

In some embodiments, the present disclosure describes fluorinated sulfonamide surfactant compositions including one or more anionic surfactants or one or more neutral surfactants, and a solvent. Suitable anionic surfactants for the surfactant compositions include those having the following structure:

$R_fSO_2N(H)$—$CH_2CH(CH_3)OH$; and
$R_fSO_2N(H)$—$(CH_2CH_2O)_xH$, where x is an integer from 2-6, 2-5, 2-4, or 2-3. Suitable neutral surfactants for the compositions include those having the following structure:

$R_fSO_2N[CH_2CH(CH_3)OH]_2$;
$R_fSO_2N[CH_2CH(CH_3)OH][(CH_2CH_2O)_nH]$, where n is an integer from 1-6, 1-5, 1-4, or 1-3;
$R_fSO_2N(R)[(CH_2CH_2O)_pH]$, where p is an integer from 2-6, 2-5, 2-4, or 2-3, and R is an alkyl group having 1 to 4 carbon atoms; and
$R_fSO_2N[(CH_2CH_2O)_qH][(CH_2CH_2O)_mH]$, where q is an integer from 1-6, 1-5, 1-4, or 1-3, m is an integer from 1-6, 1-5, 1-4, or 1-3, and (q+m)≥3.

To facilitate maximum solubility in water, in various embodiments, at least one of the non-fluorinated groups bound to the sulfonamide nitrogen atom of either the anionic or neutral surfactant may be an oligomeric ethylene oxide group, wherein the oligomeric ethylene oxide group has 2-6, 2-5, 2-4, or 2-3 ethylene oxide repeat units.

In some embodiments, the present disclosure describes fluorinated sulfonamide mixed surfactant compositions including at least one anionic surfactant, at least one neutral surfactant, and a solvent. Suitable anionic surfactants for the mixed surfactant compositions include those having the following structure:

$R_fSO_2N(H)$—$CH_2CH(CH_3)OH$;
$R_fSO_2N(H)$—$(CH_2CH_2O)_xH$, where x is an integer from 2-6, 2-5, 2-4, or 2-3; and
$R_fSO_2N(H)$—$CH_2CH_2OH$.

Suitable neutral surfactants for the mixed surfactant compositions include those having the following structure:

$R_fSO_2N[CH_2CH(CH_3)OH]_2$;
$R_fSO_2N[CH_2CH(CH_3)OH][(CH_2CH_2O)_nH]$, where n is an integer from 1-6, 1-5, 1-4, or 1-3;
$R_fSO_2N(R)[(CH_2CH_2O)_pH]$, where p is an integer from 2-6, 2-5, 2-4, or 2-3 and R is an alkyl group having 1 to 4 carbon atoms;
$R_fSO_2N[(CH_2CH_2O)_qH][(CH_2CH_2O)_mH]$, where q is an integer from 1-6, 1-5, 1-4, or 1-3, m is an integer from 1-6, 1-5, 1-4, or 1-3, and (q+m)≥3; and
$R_fSO_2N[CH_2CH_2OH]_2$.

In one embodiment, a fluorinated sulfonamide mixed surfactant composition may include appreciable amounts of (i.e. >5% by weight of the total fluorinated surfactant present on a 100% solids basis) only one anionic surfactant and only one neutral surfactant. In such an embodiment, if the anionic surfactant is $R_fSO_2N(H)$—$CH_2CH_2OH$, then the neutral surfactant is not $R_fSO_2N[CH_2CH_2OH]2$.

For the above-described fluorinated sulfonamide surfactant compositions (including the mixed surfactant compositions), each $R_f$ may independently be a fluroalkyl group having 3 to 8 carbon atoms. The fluoroalkyl group may be straight chain, branched chain, or cyclic, and may be saturated or unsaturated. The fluoroalkyl group chain may be interrupted by catenary heteroatoms (e.g., O and N). The fluoroalkyl group may have any degree of fluorination. In various embodiments, $R_f$ may be a fluoroalkyl group having 4 to 6 carbon atoms. In further embodiments, $R_f$ may be a saturated perfluoroalkyl group having 4 to 6 carbon atoms. Still further, $R_f$ may be a saturated perfluoroalkyl group having 4 carbon atoms.

To facilitate maximum solubility in water, in various embodiments, at least one of the non-fluorinated groups bound to the sulfonamide nitrogen atom of either the anionic or neutral surfactant may be an oligomeric ethylene oxide group, wherein the oligomeric ethylene oxide group has 2-6, 2-5, 2-4, or 2-3 ethylene oxide repeat units.

In some embodiments, the fluorinated sulfonamide surfactants of the present disclosure may include one or more of the compounds listed in Table 1. In various embodiments, the fluorinated sulfonamide surfactant compositions of the present disclosure may include one or more of the fluorinated sulfonamide surfactants listed in Table 1.

TABLE 1

| Structure #, Acronym | |
|---|---|
| I, H-FBSP | 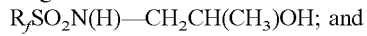 |
| II, FBSPP | 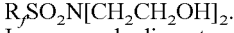 |
| III, H-FBS(EE) |  |

TABLE 1-continued

Structure #,
Acronym

IV, FBS(EE)2

V, FBSE(EE)

VI, Me-FBS(EE)

VII, Pr-FBS(EE)

VIII, H-FBS(EEE)

IX, FBS(EEE)2

X, FBSPE

In various embodiments, suitable solvents for the fluorinated sulfonamide surfactant compositions of the present disclosure may include water and/or any organic solvents that provide adequate surfactant solubility at the surfactant loading level required for acceptable performance. Single solvents or solvent mixtures may be employed. In some embodiments, the solvent may include water and one or more alcohol base chemicals, such as those described in U.S. Patent Application Pub. No. 2008/0280230.

In illustrative embodiments, the fluorinated sulfonamide surfactants may be present in solution (i.e., in water or in a mixed solvent of water and an organic solvent) at a total concentration (i.e., all fluorinated sulfonamide surfactant species included) of between 0.001% to 5.0% by mass, 0.01% to 1.0% by mass, or even 0.1% to 0.5% by mass.

In some embodiments, the fluorinated sulfonamide surfactant compositions of the present disclosure may further include one or more additives to facilitate performance in a particular application. For example, in buffered oxide etch (BOE) applications, additives may include $NH_4F$ and HF. As another example, in photoresist developer or developer rinse applications, additives may include $Me_4NOH$, $Bu_4NOH$, and/or $NH_4OH$. Still further, when used as wetting or leveling agents in coating applications, coating polymers and other additives may be added to improve coating performance.

The fluorinated sulfonamide surfactants and surfactant compositions of the present disclosure provide a number of surprising advantages compared to known surfactants. For example, the surfactants and surfactant compositions of the present disclosure exhibit improved water solubility, which can be important to reducing the possibility of surfactant precipitation during semiconductor processing and associated defect formation. As a specific example, it was discovered that anionic and neutral fluorinated sulfonamide surfactants of the present disclosure that have oligomeric ethylene oxide groups [—(CH$_2$CH$_2$O)$_n$, where n>1] bound to the sulfonamide nitrogen atom provide significantly higher solubility in water compared to known sulfonamide surfactants.

In various embodiments, the neutral surfactants and mixed surfactants of the present disclosure may exhibit surprisingly higher water solubility than known neutral or mixed surfactants. The neutral surfactants of the present disclosure may exhibit solubility in water (e.g., 18 megaohm water, at 25° C.) of at least 0.02%, at least 0.06%, or even at least 0.1%. The mixed surfactants of the present disclosure may exhibit a water solubility of at least 0.1%, at least 0.4%, or even at least 0.8%.

Additionally surprising is that the fluorinated sulfonamide surfactants of the present disclosure provide lower surface tensions in aqueous solution than similar surfactants and surfactant mixtures known in the art. This parameter can be important in advanced photolithographic processes to reducing the incidence of pattern collapse during the development or post development rinse steps. As a specific example, it was discovered that very low surface tensions can be achieved in water by controlling the pH of surfactant compositions comprising the anionic surfactants of the present disclosure. pH is generally controlled within about ±3 pH units of the pKa of the fluorinated anionic sulfonamide surfactant in order to achieve optimum performance. Furthermore, a synergy was discovered wherein lower surface tensions or improved solubilities can be achieved in water by combining the anionic and neutral surfactants of the present disclosure, relative to the individual surfactant components alone.

In some embodiments, the neutral surfactants of the present disclosure may exhibit a surface tension of no more than 30 dyn/cm, no more than 24 dyn/cm, or even no more than 20 dyn/cm as measured using the Surface Tension Test Method, described below; and the mixed surfactants may exhibit a surface tension of no more than 30 dyn/cm, no more than 24 dyn/cm, or even no more than 20 dyn/cm, as measured using the Surface Tension Test Method, described below.

Further surprising is that the fluorinated sulfonamide surfactants of the present disclosure, when used in aqueous photoresist rinse solutions, can provide additional flexibility in fine tuning the level of absorption of surfactant onto or into the photoresist material. As a specific example, it was discovered that by adjusting the pH of surfactant compositions that include one or more anionic surfactants of the present disclosure and/or altering the choice and relative ratios of the anionic and neutral surfactants of the present disclosure, a significant impact on the mass of surfactant absorbed from solution onto or into the photoresist material can be achieved. It is generally known in the art that such surfactant absorption can affect contact angles of aqueous rinse solutions on the resist surface, and influence key lithography performance attributes, such as defectivity (e.g., watermarks and particle defects), line width roughness, line edge roughness, line melting, and process window.

The present disclosure further relates to methods of making the above described fluorinated sulfonamide surfactants. In some embodiments, such methods may include deprotonating a fluorochemical sulfonamide containing at least one acidic N—H group with a base to form a fluorochemical sulfonamide anion, which can then nucleophilically attack an electrophilic reagent containing a leaving group (E), as in Scheme I below. Since the protons of a fluorochemical sulfonamide are acidic due to electron withdrawal by the fluoroalkylsulfonyl group, a variety of different bases can be used to facilitate deprotonation, such as alkali metal carbonates, organic amines, or alkali metal alkoxides. The electrophilic reagent can, for example, be an alkyl or polyoxyalkyl halide (where the halide is chloride or bromide or iodide), or a cyclic epoxide (like ethylene oxide or propylene oxide) or a cyclic organic carbonate reagent (like ethylene carbonate or propylene carbonate) that ring opens, with or without oligomerization. In the case of the cyclic organic carbonate reagents, CO$_2$ byproduct may be released in the course of the ring opening reaction. Scheme I below illustrates a non-limiting example of a process that may be used to append a polyethylene oxide chain to a fluorinated sulfonamide N atom. However, it is to be appreciated that other routes, including those described in the Examples section of the present disclosure, may be employed.

Scheme 1

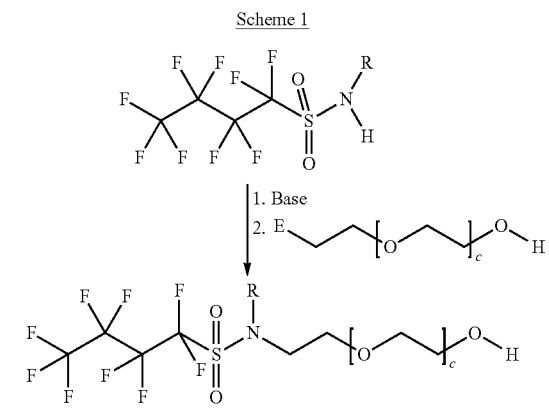

The present disclosure further relates to methods of making the above described fluorinated sulfonamide surfactant compositions. Such methods may include first adding aqueous ammonia to water to form a solution. One example of a commercially suitable ammonia includes, but is not limited to, product number 3265-45, 28-30% ammonia in water, available from Mallinkrodt Chemicals. In one embodiment, the water is 18.2 MΩ water. Fluoroalkyl sulfonamide may then be charged to the solution to make an aqueous fluoroalkyl sulfonamide solution. The solutions may be mixed for about one hour and allowed to settle overnight. The solution may then be filtered to remove insoluble material and particles. In one embodiment, the filter membrane may be polytetrafluoroethylene (PTFE), polyethylene (PE), polyether sulfone (PES), or glass fiber. In one embodiment, the filter is at least a 1 μm rating and particularly at least a 0.2 μm rating.

Generally, a process of forming a photoresist pattern on a substrate (e.g., semiconductor wafer) may include forming a resist layer over or on the substrate or wafer. Next, the resist layer may be exposed using a lithography tool, optionally followed by a post-exposure bake step. Accordingly, the desired pattern can be initially transferred to the resist layer. The method may then include developing the exposed resist layer by immersing the substrate in or otherwise subjecting the substrate to a developer fluid. Optionally, the method may then include rinsing the developed photoresist material with deionized (DI) water.

In some embodiments, the present disclosure further relates to methods of treating the surface of a photoresist material. In this regard, the methods of the present disclosure may include carrying out the above-described developing step by incorporating the fluorinated sulfonamide surfactants or surfactant compositions into the developer fluid. Additionally, or alternatively, the methods of the present disclosure may include carrying out a fluorinated sulfonamide surfactant rinse step in lieu of, prior to, or subsequent to the above-described DI water rinsing step. The fluorinated sulfonamide surfactant rinse may include one or more fluorinated sulfonamide surfactants or surfactant compositions of the present disclosure.

The operation of the present disclosure will be further described with regard to the following detailed examples. These examples are offered to further illustrate the various specific and preferred embodiments and techniques. It should be understood, however, that many variations and modifications may be made while remaining within the scope of the present disclosure.

EXAMPLES

Surface Tension Test Method

Surface tension was measured using a K12 process tensiometer (available from Kruss GmbH of Hamburg, Germany) using a Wilhemly plate method with a platinum PL01 plate (available from Krüss GmbH). Forty milliliters of the solution to be tested were placed in a 60 mL glass snap cap jar with an inner diameter of approximately 1.5 inches. Measurements were taken until the average of five measurements had a standard deviation less than 0.07 dyn/cm.

TABLE 2

Structures of Examples and Comparatives*

| Structure #, Acronym | Syn Ex # | Structure |
|---|---|---|
| I H-FBSP | 1 | |
| II FBSPP | 1 | |
| III H-FBS(EE) | 2 | |
| IV FBS(EE)2 | 3 | |
| V FBSE(EE) | 4 | |
| VI Me-FBS(EE) | 5 | |
| VII Pr-FBS(EE) | 6 | |

TABLE 2-continued

Structures of Examples and Comparatives*

| Structure #, Acronym | Syn Ex # | Structure |
|---|---|---|
| VIII H-FBS(EEE) | 7 | $C_4F_9SO_2N(H)CH_2CH_2OCH_2CH_2OCH_2CH_2OH$ |
| IX FBS(EEE)2 | 7 | $C_4F_9SO_2N(CH_2CH_2OCH_2CH_2OCH_2CH_2OH)_2$ |
| X FBSPE | 8 | $C_4F_9SO_2N(CH_2CH(CH_3)OH)(CH_2CH(CH_3)OH)$ |
| A H-FBSE | | $C_4F_9SO_2N(H)CH_2CH_2OH$ |
| B FBSEE | | $C_4F_9SO_2N(CH_2CH_2OH)_2$ |
| C Me-FBSE | | $C_4F_9SO_2N(CH_3)CH_2CH_2OH$ |
| D FBSA | | $C_4F_9SO_2NH_2$ |
| E FES(EE)2 | 9 | $C_2F_5SO_2N(CH_2CH_2OCH_2CH_2OH)_2$ |

*Structures of the invention have Roman numeral designations. Comparative structure examples have alphabetic letter designations.

Surfactant Synthesis Examples

Synthesis 1

$C_4F_9SO_2N(H)CH_2CH(CH_3)OH$ (I) and $C_4F_9SO_2N[CH_2CH(CH_3)OH]_2$ (II)

$C_4F_9SO_2NH_2$ (100.00 g, 0.3343 mol) (prepared as described in U.S. Pat. No. 7,169,323), $K_2CO_3$ powder (5.54 g, 0.0401 mol), and anhydrous propylene carbonate (68.26 g, 0.6687 mol) were batch charged to a 200 mL round bottom flask equipped with a Claisen adapter, water cooled condenser with nitrogen inlet line, immersion thermocouple probe, magnetic stirrer and heating mantle. The reaction mixture was gradually heated to 160° C. under nitrogen with stirring and then held at 160° C. for about 15 hours. After cooling to room temperature, an aliquot of the reaction mixture was removed and analyzed by GC in acetone. GC-FID analysis revealed the presence of about 38% $C_4F_9SO_2N(H)CH_2CH(CH_3)OH$ and 24% $C_4F_9SO_2N[CH_2CH(CH_3)OH]_2$ (mix of two diastereomers). Peak assignments were confirmed by GC-MS. To the reaction mixture was added 69.4 g of deionized water and 19.4 g of 20 wt % $H_2SO_4$(aq). After heating to 60° C. to reduce viscosity the reaction mixture was stirred vigorously to neutralize all residual base and then transferred to a separatory funnel and allowed to phase separate. The lower product phase was separated, washed with about 60 mL of additional hot water and then phase separated again. The lower product phase was isolated and then dissolved in 240 g of MTBE (methyl t-butyl ether available from Sigma-Aldrich, St Louis, Mo.) to cut viscosity and facilitate additional extractions. After filtration by gravity through fluted filter paper, the product solution in MTBE was transferred to a 1.0 L separatory funnel and extracted with three 300 mL portions of deionized (DI) water. The upper MTBE/product phase was isolated and then concentrated on a rotary evaporator at 20 Torr, 20-50° C. to remove bulk of MTBE solvent to isolate crude product.

The crude product was then fractionally distilled under vacuum (3 Torr) through a short Vigreux column to separate and isolate the two desired product fractions. Fraction #2 comprising 36.4 g of 92.1% pure $C_4F_9SO_2N(H)CH_2CH(CH_3)OH$ was collected at a head temperature of 128-133° C. Fraction #5 comprising 12.49 g of 91.7% pure $C_4F_9SO_2N[CH_2CH(CH_3)OH]_2$ (mix of two diastereomers) was collected at a head temperature of 148.0-148.5° C. The two isolated product fractions (#2 and #5) were separately dissolved in hot toluene to 20% solids, filtered hot to remove insolubles, and then allowed to cool to room temperature and recrystallize. Once recrystallization was complete, the white crystalline solids that formed were isolated by vacuum filtration, washed with toluene at room temperature (RT) and then recrystallized a second time from hot toluene at about 30% solids using a similar procedure. The isolated crystalline solids were vacuum dried at 60-65° C. for about 3 hours in a vacuum oven at about 80 mTorr to remove residual toluene and other volatiles. The final isolated yield of $C_4F_9SO_2N(H)CH_2CH(CH_3)OH$ from Fraction #2 was 27.082 g with a GC-FID purity of 98.54%. $C_4F_9SO_2N(H)CH_2CH(CH_3)OH$ was a solid with a melting point of 80.33° C. as determined by DSC. The final isolated yield of $C_4F_9SO_2N[CH_2CH(CH_3)OH]_2$ from Fraction #5 was 8.537 g with a GC-FID purity of 99.77% (approximately 50:50 mixture of two possible diastereomers). In both cases the only observable impurity was residual toluene solvent. Both purified product samples were analyzed by $^1H$, $^{19}F$ and $^{13}C$ NMR spectroscopy to determine the identities and relative quantities of the primary isomeric components. The product isolated from distillate Fraction #2 was found to contain 98.3% $C_4F_9SO_2N(H)CH_2CH(CH_3)OH$ (major isomer) and 1.7% $C_4F_9SO_2N(H)CH(CH_3)CH_2OH$ (minor isomer). Fraction #5 was found to contain 99.2% $C_4F_9SO_2N[CH_2CH(CH_3)OH]_2$ (major isomer) and 0.8% $C_4F_9SO_2N[CH_2CH(CH_3)OH][CH(CH_3)CH_2OH]$ (minor isomer). The NMR results confirm that propylene carbonate is preferably attacked by the nucleophilic sulfonamide nitrogen at the unsubstituted, secondary —$CH_2$— carbon to form the major mono-ol and diol product isomers.

Synthesis 2

$C_4F_9SO_2N(H)CH_2CH_2OCH_2CH_2OH$ (III)

$C_4F_9SO_2NH_2$ (100.00 g, 0.3343 mol) and triethylamine (101.48 g, 1.0029 mol) were batch charged to a 500 mL, 3-necked round bottom flask equipped with a Claisen adapter, addition funnel, water cooled condenser with nitrogen inlet line, immersion thermocouple probe, mechanical stirrer and heating mantle. After heating mixture to a set point of 60° C., $ClCH_2CH_2OCH_2CH_2OH$ (53.726 g, 0.4313 mol; available from Alfa Aesar, Ward Hill, Mass.) was gradually added with stirring from addition funnel over a period of 40 minutes without significant exotherm or precipitate. Reaction temperature was increased to 95° C. and held for 17 hours resulting in formation of significant white precipitate ($Et_3NH^+C_1^-$). GC analysis of an aliquot of the reaction mixture indicated that the reaction had proceeded to only 36.5% conversion, so an additional 10.00 g of $ClCH_2CH_2OCH_2CH_2OH$ was charged to the reaction mixture via syringe and the mixture was allowed to react at 95° C. for an additional 66 hours with stirring. After cooling to room temperature, an aliquot of the reaction mixture was removed for GC-FID analysis, which revealed 23.1% unreacted $C_4F_9SO_2NH_2$, 52.2% $C_4F_9SO_2N(H)CH_2CH_2OCH_2CH_2OH$ (desired product) and 24.8% of the corresponding diol, $C_4F_9SO_2N[CH_2CH_2OCH_2CH_2OH]_2$. To the cooled reaction mixture was added 69 g deionized water and 99.4 g of 20% $H_2SO_4$(aq) with stirring. The resulting mixture was transferred to a 1.0 L separatory funnel and extracted with 239 g MTBE. The lower aqueous phase was separated and drained and the remaining MTBE/product phase was washed with 300 mL of deionized water. A stable emulsion formed, which was broken by adding a small amount of concentrated aqueous NaCl and 150 mL of 42.5% phosphoric acid. After this first wash, the lower aqueous phase was drained and the remaining MTBE phase was washed two more times with a mixture of 300 mL of water and 150 ml of 42.5% phosphoric acid. A stable emulsion was formed again during the third wash, so entire contents of separatory funnel were drained into a beaker and the MTBE was allowed to evaporate. This resulted in clean phase separation of the product (lower phase) from the aqueous acid (upper phase). The lower product phase was isolated using a separatory funnel and then purified by fractional vacuum distillation at 2.0 Torr through a short Vigreux column. A total of 33.9 g of desired product, $C_4F_9SO_2N(H)CH_2CH_2OCH_2CH_2OH$, was collected in Fraction #3 at a head temperature of 136.5-143.5° C. The isolated product collected in Fraction #3 was a clear colorless viscous liquid initially, with a purity determined by GC-FID of 99.25%. GC peak assignments were confirmed by GC-MS. This material ultimately crystallized to a low melting solid with a melting point (mp) of 35.7° C.

Synthesis 3

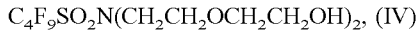

$C_4F_9SO_2N(CH_2CH_2OCH_2CH_2OH)_2$, (IV)

$C_4F_9SO_2NH_2$ (295 g, 0.9867 mol) and $ClCH_2CH_2OCH_2CH_2OH$ (491 g, 3.94 mol) were batch charged to a 1000 mL, 3-necked round bottom flask equipped with a Claisen adapter, water cooled condenser, immersion thermocouple probe, mechanical stirrer and heating mantle. After heating mixture to a set point of 90° C., potassium carbonate (300 g, 2.17 mol) was gradually added with stirring over a period of 15 minutes without significant exotherm or precipitate. Reaction temperature was increased to 120° C. and held for 17 hours. The batch temperature was lowered to 90° C. and 1000 g of hot water was added. The contents were split in a separatory funnel to give 622 g of lower fluorochemical phase. The lower phase was returned to the flask and 300 ml of water, 107 g of 86% phosphoric acid, and 53 g of sodium chloride was added and stirred with the batch, and then poured into a separatory funnel. The bottom layer was then split off to give 669 g. The lower phase was stripped at atmospheric pressure until the pot temperature reached 150° C. The batch was then cooled to 90° C., and with good stirring the stripping was continued under vacuum to remove unreacted ClCH$_2$CH$_2$OCH$_2$CH$_2$OH and C$_4$F$_9$SO$_2$NH$_2$. Stripping was begun at 90° C. and 103 mm Hg to a receiver that was cooled in dry ice/acetone and continued until the vacuum was 0.4 mm Hg and the batch had reached 100° C. The batch was cooled, vacuum was broken and the receiver was emptied. The distillation was then continued at 0.4 mm Hg. Cut 1 distilled at a head temp of 173-181° C. and a pot temp of 189-200° C., and weighed 34 g. Cut 2 distilled at 0.2 mm Hg at a head temperature of 181-182° C. and a pot temperature of 200-203° C. and weighed 118 g. Cut 3 distilled at 0.2 mm at a head temperature of 181-210° C. and a pot temperature of 207-215° C. and weighed 47 g.

NMR and GC/MS showed cut 2 to be 89.5% the desired C$_4$F$_9$SO$_2$N(CH$_2$CH$_2$OCH$_2$CH$_2$OH)$_2$ (including minor branched FC isomers), 9.8% C$_4$F$_9$SO$_2$NHCH$_2$CH$_2$OCH$_2$CH$_2$OH, 0.6% C$_4$F$_9$SO$_2$NH$_2$. GC/MS showed cut 3 to be 83.1% the desired C$_4$F$_9$SO$_2$N(CH$_2$CH$_2$OCH$_2$CH$_2$OH)$_2$ (including minor branched FC isomers).

Synthesis 4

C$_4$F$_9$SO$_2$N(CH$_2$CH$_2$OCH$_2$CH$_2$OH)(CH$_2$CH$_2$OH), (V)

C$_4$F$_9$SO$_2$NHCH$_2$CH$_2$OH (249 g, 0.725 mol; prepared according to U.S. Pat. No. 7,169,323) and ClCH$_2$CH$_2$OCH$_2$CH$_2$OH (211 g, 1.70 mol) were batch charged to a 1000 mL, 3-necked round bottom flask equipped with a Claisen adapter, water cooled condenser, immersion thermocouple probe, mechanical stirrer and heating mantle. After heating mixture to a set point of 90° C., potassium carbonate (120 g, 0.86 mol) was gradually added with stirring over a period of 15 minutes without significant exotherm or precipitate. Reaction temperature was increased to 120° C. and held for 17 hours. GC-FID analysis (in acetone) revealed the presence of about 37% unreacted ClCH$_2$CH$_2$OCH$_2$CH$_2$OH, no detectible C$_4$F$_9$SO$_2$NHCH$_2$CH$_2$OH, and 58.3% C$_4$F$_9$SO$_2$N(CH$_2$CH$_2$OCH$_2$CH$_2$OH)(CH$_2$CH$_2$OH). The batch temperature was lowered to 90° C. and 230 g of hot water was added. After addition of water 18 g of 85% phosphoric acid was added to the batch. The contents were phase split in a separatory funnel to give 385 g of lower fluorochemical phase. The lower phase was returned to the flask and 100 ml of water, and 40 g of 86% phosphoric acid, were added and stirred with the batch. After sitting for an hour, no phase split could be seen. 377 g of methyl t-butyl ether was added to the batch, which was allowed to stir for 15 min. After the phase split, 759 g of methyl t-butyl ether product solution was separated from 166 g of lower aqueous phase. The ether solution was stripped at atmospheric pressure until the batch temperature reached 77° C. The batch was further stripped at 8.6 mm Hg until the pot temperature reached 132° C., and then the receiver was emptied. Then stripping was continued until the pressure reached 2.2 mm Hg at a head temperature of 171° C. The receiver was then emptied and collection of the product cut was begun at 0.2 mm Hg vacuum and a head temperature of 172° C. and a pot temperature of 184° C. Distillation was continued until the pot reached 195° C. to give 183 g of distillate. GC-FID analysis of the distillate showed the material to be 95.4% desired product (V). At room temperature the material crystallized to a low melting solid with a melting point of 45.1° C. as determined by DSC.

Synthesis 5

C$_4$F$_9$SO$_2$N(CH$_3$)(CH$_2$CH$_2$OCH$_2$CH$_2$OH), (VI)

C$_4$F$_9$SO$_2$NHCH$_3$ (339 g, 1.087 mol) (prepared as described in U.S. Pat. No. 6,852,781) and ClCH$_2$CH$_2$OCH$_2$CH$_2$OH (314 g, 2.52 mol) were batch charged to a 2000 mL, 3-necked round bottom flask equipped with a Claisen adapter, water cooled condenser, immersion thermocouple probe, mechanical stirrer and heating mantle. After heating the mixture to a set point of 90° C., potassium carbonate (179 g, 1.29 mol) was gradually added with stirring over a period of 15 minutes without significant exotherm or precipitate. Reaction temperature was increased to 120° C. and held for 17 hours. GC-FID analysis in acetone after overnight heating at 120° C. revealed the presence of about 30% unreacted ClCH$_2$CH$_2$OCH$_2$CH$_2$OH, no detectible C$_4$F$_9$SO$_2$NHCH$_3$, and 58.9% C$_4$F$_9$SO$_2$N(CH$_3$)(CH$_2$CH$_2$OCH$_2$CH$_2$OH). The batch temperature was lowered to 90° C. and 300 g of hot water was added. After addition of water, 100 g of 85% phosphoric acid was added to the batch. The contents were phase split in a separatory funnel to give 523 g of lower fluorochemical phase. The bottom fluorochemical phase was stripped at atmospheric pressure until the batch temperature reached 140° C. The batch was further stripped at 63 mm Hg until the pot temperature reached 101° C., and then the receiver was emptied. Then stripping was continued until the pressure reached 2.2 mm Hg and 152° C. The receiver was emptied and collection of the product cut was begun at 0.2 mm Hg vacuum, at a head temperature of 125° C. and a pot temperature of 149° C. Distillation was continued until the head temperature was 132° C., and the pot temperature reached 152° C. to give 363 g of material. GC-FID analysis showed the material to be 97.8 area % the desired product. C$_4$F$_9$SO$_2$N(CH$_3$)(CH$_2$CH$_2$OCH$_2$CH$_2$OH) was found to be a solid at room temperature with a melting point of 80.5° C. as determined by DSC. The chemical structure of this material was confirmed to be (VI) by $^1$H and $^{19}$F NMR analysis.

Synthesis 6

C$_4$F$_9$SO$_2$N(n-C$_3$H$_7$)(CH$_2$CH$_2$OCH$_2$CH$_2$OH), (VII)

C$_4$F$_9$SO$_2$NH(n-C$_3$H$_7$) (382 g, 1.137 mol) (prepared as described in U.S. Pat. No. 7,572,848) and ClCH$_2$CH$_2$OCH$_2$CH$_2$OH (328 g, 2.63 mol) were batch charged to a 2000 mL, 3-necked round bottom flask equipped with a Claisen adapter, water cooled condenser, immersion thermocouple probe, mechanical stirrer and heating mantle. After heating mixture to a set point of 90° C., potassium carbonate (184 g, 1.33 mol) was gradually added with stirring over a period of 15 minutes without significant exotherm or precipitate. Reaction temperature was increased to 120° C. and held for 17 hours. GC analysis in acetone after overnight heating at 120° C. revealed the presence of about 31% unreacted ClCH$_2$CH$_2$OCH$_2$CH$_2$OH, no detectible C$_4$F$_9$SO$_2$NH(n-C$_3$H$_7$), and 67.2 area % C$_4$F$_9$SO$_2$N(n-C$_3$H$_7$)(CH$_2$CH$_2$OCH$_2$CH$_2$OH). The batch temperature was lowered to 90° C. and 380 g of hot water was added. After addition of water, 100 g of 85% phosphoric acid was added to the batch. The contents were phase split in a separatory funnel and the lower fluorochemical phase was isolated. The fluorochemical phase was stripped at atmospheric pressure until the batch temperature reached 110° C. The batch was further stripped at 28 mm Hg until the pot temperature reached 140° C., and then the receiver was emptied. Distillation was continued at an initial pressure of 2.6 mm Hg until the head temperature reached 142° C., and the pot temperature reached 164° C. and the pressure dropped to 0.6 mm Hg to give 430 g of distillate. GC-FID analysis showed the collected distillate to be 100 area % desired product. The chemical structure of this material was confirmed to be (VII) by $^1$H and $^{19}$F NMR analysis.

Synthesis 7

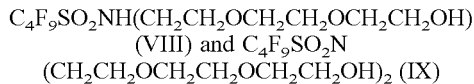
(VIII) and $C_4F_9SO_2N$
$(CH_2CH_2OCH_2CH_2OCH_2CH_2OH)_2$ (IX)

$C_4F_9SO_2NH_2$ (640 g, 2.14 mol) and $ClCH_2CH_2OCH_2CH_2OCH_2CH_2OH$ (288 g, 1.71 mol, available from Aldrich, St. Louis, Mo.) were batch charged to a 2000 mL, 3-necked round bottom flask equipped with a Claisen adapter, water cooled condenser, immersion thermocouple probe, mechanical stirrer and heating mantle. After heating mixture to a set point of 90° C., sodium carbonate (189 g, 1.81 mol) was gradually added with stirring over a period of 15 minutes without significant exotherm or precipitate. Reaction temperature was increased to 120° C. and held for 17 hours. The batch temperature was lowered to 90° C. and 750 g of hot water was added followed by 103 g of 85% phosphoric acid. The contents were phase split in a separatory funnel. The lower fluorochemical phase was returned to the flask and 508 ml of water, 53 g of 86% phosphoric acid, and 53 g of sodium chloride were added and stirred with the batch, and then poured back into a separatory funnel. The bottom layer was then phase split off to give 888 g of crude product. An aliquot of the washed crude was removed and analyzed by GC-FID in acetone revealing the presence of about 22% unreacted $C_4F_9SO_2NH_2$, 60% $C_4F_9SO_2NH$ $(CH_2CH_2OCH_2CH_2OCH_2CH_2OH)$ and 21% $C_4F_9SO_2N$ $(CH_2CH_2OCH_2CH_2OCH_2CH_2OH)_2$. The crude product mixture was stripped at atmospheric pressure until the pot temperature reached 150° C. The batch was then cooled to 90° C., and with good stirring the stripping was continued under vacuum to remove unreacted $ClCH_2CH_2OCH_2CH_2OCH_2CH_2OH$ and $C_4F_9SO_2NH_2$. Stripping was begun at 90° C. and 103 mm Hg to a receiver that was cooled in dry ice/acetone and continued until the pressure dropped to 0.4 mm Hg and the batch had reached 100° C. The batch was cooled, vacuum was broken and the receiver was emptied. The distillation was then continued at 0.4 mm Hg pressure. Cut 1 distilled at a head temp of 136-158° C. and a pot temp of 163-174° C. Cut 2 distilled at 0.2 mm Hg at a head temperature of 140-180° C. and a pot temperature of 174-195° C. and weighed 282 g. Cut 3 distilled at 0.2 mm Hg at a head temperature of 181-193° C. and a pot temperature of 193-215° C. and weighed 69 g. GC-FID analysis of Cut 2 revealed the presence of 97.2% $C_4F_9SO_2NH(CH_2CH_2OCH_2CH_2OCH_2CH_2OH)$ (VIII) and 2.8% $C_4F_9SO_2N(CH_2CH_2OCH_2CH_2OCH_2CH_2OH)_2$ (IX), and was a white solid at room temperature with a melting point of 58.5° C. GC-FID analysis of Cut 3 revealed the presence of 66% $C_4F_9SO_2NH$ $(CH_2CH_2OCH_2CH_2OCH_2CH_2OH)$ (VIII) and 33.3% $C_4F_9SO_2N(CH_2CH_2OCH_2CH_2OCH_2CH_2OH)_2$ (IX). Cut 3 was a thick yellow liquid at room temperature. The chemical structure of the major product collected in cut 2 was confirmed to be (VIII) by $^1$H and $^{19}$F NMR analysis.

Synthesis 8

$C_4F_9SO_2NHCH_2CH_2OH$ (500.00 g, 1.43 mol), $K_2CO_3$ powder (53 g, 0.39 mol), and anhydrous propylene carbonate (500 g, 4.9 mol) were batch charged to a 1.0 L round bottom 3-necked flask equipped with a Claisen adapter, water cooled condenser with nitrogen inlet line, immersion thermocouple probe, overhead stirrer and heating mantle. The reaction mixture was gradually heated to 130° C. It was heated and stirred overnight. After cooling to 84° C., an aliquot of the reaction mixture was removed and analyzed by GC in acetone. GC-FID analysis revealed the presence of about 56 area % unreacted propylene carbonate, 2.65% $C_4F_9SO_2N(H)CH_2CH_2OH$ and 32.6% $C_4F_9SO_2NCH_2CH_2OH$ [$CH_2CH(CH_3)OH$]. At 84° C., 800 ml of water was added to the batch followed by slow addition of 100 g of 85% phosphoric acid. The batch was phase split in a separatory funnel to give 884 g of lower crude fluorochemical product. The lower phase was washed with 500 g of water with 10 g of NaCl dissolved in it to give 773 g of lower fluorochemical layer. The fluorochemical phase was stripped at atmospheric pressure until the pot temperature reached 100° C., giving 160 g of distillate. A precut was collected by distilling under vacuum (57 to 2 mm Hg) when the pot temperature was 35-143° C. A second precut was distilled at 2 to 1.4 mm Hg with a pot temperature of 143-183° C. and a head temperature of 105-152° C., resulting in the collection of 62 g of distillate. GC analysis of this second precut by GC-FID showed it to be 11.3 area % H-FBSE and 72% the desired product (X). The main product cut was distilled at 1.4 to 0.2 mm Hg at a pot temp of 183-215° C. and a head temperature of 150-160° C., yielding 308 g of distillate. GC analysis showed this material to be 70.6% desired product. Recrystallization of the distilled main cut from toluene led to material that was 98.4% desired product (X) by GC-FID.

Synthesis 9

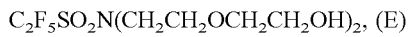

$C_2F_5SO_2NH_2$ (55.7 g, 0.279 mol; prepared according to the procedure for $C_4F_9SO_2NH_2$ as described in U.S. Pat. No. 7,169,323 with the exception that $C_4F_9SO_2F$ was replaced with $C_2F_5SO_2F$) and $ClCH_2CH_2OCH_2CH_2OH$ (175 g, 1.4 mol) were batch charged to a 1000 mL, 3-necked round bottom flask equipped with a Claisen adapter, water cooled condenser, immersion thermocouple probe, mechanical stirrer and heating mantle. After heating mixture to a set point of 90° C., potassium carbonate (113 g, 0.81 mol) was gradually added with stirring over a period of 15 minutes without significant exotherm or precipitate. Reaction temperature was increased to 120° C. and held for 17 hours. The batch temperature was lowered to 90° C. and 250 g of hot water and 33 g of 86% phosphoric acid were added. The contents were split in a separatory funnel to give 206 g of lower fluorochemical phase. GC-FID analysis of the lower fluorochemical phase (in acetone) revealed the presence of 54.8% $ClCH_2CH_2OCH_2CH_2OH$ plus $C_2F_5SO_2NH_2$ and 38.8% of the desired product (area %). The lower fluorochemical phase was stripped at atmospheric pressure until the pot temperature reached 150° C. The batch was then cooled to 90° C., and with good stirring the stripping was continued under vacuum to remove unreacted $ClCH_2CH_2OCH_2CH_2OH$ and $C_2F_5SO_2NH_2$. Stripping was begun at 90° C. and 103 mm Hg to a receiver that was cooled in dry ice/acetone and continued until the vacuum was 2.5 mm Hg and the batch temperature had reached 100° C. The batch was then cooled, vacuum was broken and the receiver was emptied. The distillation was then continued at 2.5 mm Hg. Cut 1 distilled at a head temp of 146-148° C. and a pot temp of 189-206° C., and weighed 57 g. Cut 2 distilled at 0.2-2.0 mm Hg at a head temperature of 159-180° C. and a pot temperature of 185-203° C. and weighed 13.3 g. GC-FID analysis of Cut 1 (in acetone) revealed it was 93.6 area % desired product (E). Cut 2 was similarly analyzed and found to be 89.8 area % desired product (E).

Surfactant Performance Testing Examples

Examples 1-4

Solubility and Surface Tension of H-FBSP (I) with Ammonium Hydroxide

25% solutions of H-FBSP were prepared by dissolving molten H-FBSP in aqueous ammonium hydroxide (29% NH3 in water available from KMG Chemicals, Houston, Tex.) which had been diluted with 18.2 megaohm DI water. The mole ratio—defined as the moles of base to the moles of fluorochemical surfactant—was varied. The solutions were mixed for one hour and allowed to settle over night. Examples were prepared as described in Table 3.

TABLE 3

Sample Preparation of H-FBSP in Aqueous NH$_4$OH

| Example | Mole Ratio | Mass Water (g) | Mass 29% NH$_3$ (g) | Mass H-FBSP (g) | Soluble |
|---|---|---|---|---|---|
| 1 | 2.0 | 3.357 | 0.396 | 1.256 | Yes |
| 2 | 1.5 | 3.443 | 0.299 | 1.250 | Yes |
| 3 | 1.0 | 3.552 | 0.208 | 1.249 | No |
| 4 | 0.5 | 3.649 | 0.109 | 1.249 | No |

The homogeneous solutions were diluted in water for surface tension and solubility measurements. Surface tension and solubility results are summarized in Table 4.

TABLE 4

H-FBSP in Aqueous NH$_4$OH Diluted in Water

| Sample | Concentration (ppm) | Surface Tension (dyn/cm) | Soluble |
|---|---|---|---|
| Example 1 Mole Ratio 2.0 | 2000 | 51.6 | Yes |
|  | 4000 | 46.2 | Yes |
|  | 6000 | 42.8 | Yes |
|  | 8000 | 40.5 | Yes |
| Example 2 Mole Ratio 1.5 | 2000 | 47.9 | Yes |
|  | 4000 | 41.6 | Yes |
|  | 6000 | 37.9 | Yes |
|  | 8000 | 35.6 | Yes |

Examples 5-8

Solubility and Surface Tension of H-FBS(EE) (III) with Ammonium Hydroxide

25% solutions of H-FBS(EE) were prepared by dissolving the H-FBS(EE) liquid in aqueous ammonium hydroxide which had been diluted with 18.2 megaohm water. The solutions were mixed for one hour and allowed to settle over night. Examples were prepared as described in Table 5.

TABLE 5

Sample Preparation of H-FBS(EE) in Aqueous NH$_4$OH

| Example | Mole Ratio | Mass Water (g) | Mass 29% NH$_3$ (g) | Mass H-FBS(EE) (g) | Soluble |
|---|---|---|---|---|---|
| 5 | 2.0 | 2.692 | 0.305 | 0.998 | Yes |
| 6 | 1.5 | 2.773 | 0.231 | 0.999 | Yes |
| 7 | 1.0 | 2.854 | 0.153 | 0.992 | Yes |
| 8 | 0.5 | 2.915 | 0.077 | 0.993 | Yes |

The solutions were diluted in water for surface tension and solubility measurements. The results are summarized in Table 6.

TABLE 6

H-FBS(EE) in Aqueous NH$_4$OH Diluted in Water

| Sample | Concentration (ppm) | Surface Tension (dyn/cm) | Soluble |
|---|---|---|---|
| Example 5 Mole Ratio 2.0 | 1000 | 47.9 | Yes |
|  | 2000 | 42.1 | Yes |
|  | 4000 | 35.5 | Yes |
|  | 6000 | 32.9 | Yes |
|  | 8000 | 30.4 | Yes |
| Example 6 Mole Ratio 1.5 | 1000 | 46.6 | Yes |
|  | 2000 | 41.1 | Yes |
|  | 4000 | 34.5 | Yes |
|  | 6000 | 31.4 | Yes |
|  | 8000 | 28.8 | Yes |
| Example 7 Mole Ratio 1.0 | 1000 | 36.8 | Yes |
|  | 2000 | 30.3 | Yes |
|  | 4000 | 24.1 | Yes |
|  | 6000 | 21.1 | Yes |
|  | 8000 | 20.1 | Yes |
| Example 8 Mole Ratio 0.5 | 1000 | 29.4 | Yes |
|  | 2000 | 24.7 | 2$^{nd}$ Liquid Phase |
|  | 4000 | 21.0 | 2$^{nd}$ Liquid Phase |

Examples 9-12

Solubility and Surface Tension of H-FBS(EE) (III) with Tetramethyl Ammonium Hydroxide 25% solutions of H-FBS(EE) were prepared by dissolving the H-FBS(EE) liquid in aqueous tetramethylammonium hydroxide (TMAH, 25% TMAH in water available from Alfa Aesar, Ward Hill, Mass.) which had been diluted with 18.2 megaohm water. The solutions were mixed for one hour and allowed to settle over night. Examples were prepared as described in Table 7.

TABLE 7

Sample Preparation of H-FBS(EE) in Aqueous TMAH

| Example | Mole Ratio | Mass Water (g) | Mass 25% TMAH (g) | Mass H-FBS(EE) (g) | Soluble |
|---|---|---|---|---|---|
| 9 | 2.0 | 1.401 | 2.351 | 1.258 | Yes |
| 10 | 1.5 | 1.989 | 1.761 | 1.248 | Yes |
| 11 | 1.0 | 2.573 | 1.183 | 1.248 | Yes |
| 12 | 0.5 | 3.153 | 0.597 | 1.260 | Yes |

The solutions were diluted in water for surface tension and solubility measurements. The results are summarized in Table 8.

TABLE 8

H-FBS(EE) in Aqueous TMAH Diluted in Water

| Sample | Concentration (ppm) | Surface Tension (dyn/cm) | Soluble |
|---|---|---|---|
| Example 9 | 1000 | 46.4 | Yes |
| Mole Ratio 2.0 | 2000 | 41.4 | Yes |
| | 4000 | 35.8 | Yes |
| | 6000 | 32.4 | Yes |
| | 8000 | 30.3 | Yes |
| Example 10 | 1000 | 46.5 | Yes |
| Mole Ratio 1.5 | 2000 | 41.0 | Yes |
| | 4000 | 35.7 | Yes |
| | 6000 | 32.5 | Yes |
| | 8000 | 30.0 | Yes |
| Example 11 | 1000 | 45.4 | Yes |
| Mole Ratio 1.0 | 2000 | 40.6 | Yes |
| | 4000 | 34.7 | Yes |
| | 6000 | 32.4 | Yes |
| | 8000 | 29.5 | Yes |
| Example 12 | 1000 | 28.2 | Yes |
| Mole Ratio 0.5 | 1500 | 24.1 | No |
| | 2000 | 23.4 | No |
| | 4000 | 20.3 | No |

Examples 13-16

Solubility and Surface Tension of H-FBS(EEE) (VIII) with Ammonium Hydroxide

25% solutions of H-FBS(EEE) were prepared by dissolving molten H-FBS(EEE) in aqueous ammonium hydroxide which had been diluted with 18.2 megaohm water. The solutions were mixed for one hour and allowed to settle over night. Examples were prepared as described in Table 9.

TABLE 9

Sample Preparation of H-FBS(EEE) in Aqueous NH$_4$OH

| Example | Mole Ratio | Mass Water (g) | Mass 29% NH$_3$ (g) | Mass H-FBS(EEE) (g) | Soluble |
|---|---|---|---|---|---|
| 13 | 2.0 | 6.795 | 0.696 | 2.503 | Yes |
| 14 | 1.5 | 6.972 | 0.533 | 2.513 | Yes |
| 15 | 1.0 | 7.151 | 0.347 | 2.502 | Yes |
| 16 | 0.5 | 7.325 | 0.178 | 2.498 | Yes |

The solutions were diluted in water for surface tension and solubility measurements. The results are summarized in Table 10.

TABLE 10

H-FBS(EEE) in Aqueous NH$_4$OH Diluted in Water

| Sample | Concentration (ppm) | Surface Tension (dyn/cm) | Soluble |
|---|---|---|---|
| Example 13 | 1000 | 39.9 | Yes |
| Mole Ratio 2.0 | 2000 | 35.2 | Yes |
| | 4000 | 31.4 | Yes |
| | 6000 | 29.2 | Yes |
| | 8000 | 27.6 | Yes |
| Example 14 | 1000 | 38.7 | Yes |
| Mole Ratio 1.5 | 2000 | 33.3 | Yes |
| | 4000 | 29.4 | Yes |

TABLE 10-continued

H-FBS(EEE) in Aqueous NH$_4$OH Diluted in Water

| Sample | Concentration (ppm) | Surface Tension (dyn/cm) | Soluble |
|---|---|---|---|
| | 6000 | 26.6 | Yes |
| | 8000 | 25.4 | Yes |
| Example 15 | 1000 | 34.0 | Yes |
| Mole Ratio 1.0 | 2000 | 28.4 | Yes |
| | 4000 | 24.5 | Yes |
| | 6000 | 22.5 | Yes |
| | 8000 | 20.8 | Yes |
| Example 16 | 1000 | 26.5 | Yes |
| Mole Ratio 0.5 | 1500 | 23.8 | Yes |
| | 2000 | 23.2 | Yes |
| | 3000 | 21.2 | No |
| | 4000 | 21.6 | No |

Examples 17 & 18

Solubility and Surface Tension of H-FBSP (I) Blends in Ammonium Hydroxide

Blends of 22% H-FB SP and 3% of a neutral surfactant were made by dissolving molten H-FBSP with the following neutral surfactants—FBSEE (B; prepared as described in U.S. Patent Application Pub. No. 2010/0160458) or FBSPP (II), in aqueous ammonium hydroxide which had been diluted in 18.2 megaohm water. The solutions were mixed for one hour and allowed to settle over night. Examples were prepared as described in Table 11.

TABLE 11

Sample Preparation of H-FBSP + Neutral Surfactants in Aqueous NH$_4$OH

| Example | 17 | 18 |
|---|---|---|
| Neutral | FBSEE | FBSPP |
| Mass Water (g) | 3.348 | 3.351 |
| Mass 29% NH$_3$ (g) | 0.397 | 0.399 |
| Mass H-FBSP (g) | 1.103 | 1.102 |
| Mass Neutral (g) | 0.154 | 0.151 |
| Soluble | Yes | Yes |

The solutions were diluted in water for surface tension and solubility measurements. The results are summarized in the Table 12.

TABLE 12

H-FBSP + Neutral Surfactants in Aqueous NH$_4$OH Diluted in Water

| Sample | Concentration (ppm) | Surface Tension (dyn/cm) | Soluble |
|---|---|---|---|
| Example 17 FBSEE | 2000 | 30.5 | Yes |
| Example 18 FBSPP | 500 | 35.4 | Yes |
| | 1000 | 31.2 | Light Precipitate |
| | 2000 | 26.6 | Precipitate |

Examples 19-23

Solubility and Surface Tension of H-FBS(EE) (III) Blends in Ammonium Hydroxide

Blends of 22% H-FBS(EE) and 3% of a neutral surfactant were made by dissolving H-FBS(EE) with each of the following neutral surfactants—FB SEE (B; prepared as described in U.S. Patent Application Pub. No. 2010/0160458), FBS(EE)2 (IV), FBSPE (X), FBSE(EE) (V) or Pr-FBS(EE) (VII). Solutions were prepared in aqueous ammonium hydroxide which had been diluted in 18.2 megaohm water. The solutions were mixed for one hour and allowed to settle over night. Examples were prepared as described in Table 13.

TABLE 13

Sample Preparation of H-FBS(EE) + Neutral Surfactants in Aqueous NH$_4$OH

| Example | 19 | 20 | 21 | 22 | 23 |
|---|---|---|---|---|---|
| Neutral | FBSEE | FBS(EE)2 | FBSPE | Me-FBS(EE) | Pr-FBS(EE) |
| Mass Water (g) | 2.699 | 2.699 | 6.734 | 6.748 | 2.696 |
| Mass 29% NH$_3$ (g) | 0.296 | 0.296 | 0.764 | 0.752 | 0.306 |
| Mass H-FBS(EE) (g) | 0.886 | 0.880 | 2.204 | 2.212 | 0.883 |
| Mass Neutral (g) | 0.116 | 0.119 | 0.301 | 0.303 | 0.117 |
| Soluble | Yes | Yes | Yes | Yes | Yes |

The solutions were diluted in water for surface tension and solubility measurements. The results are summarized in Table 14.

TABLE 14

H-FBS(EE) + Neutral Surfactants in Aqueous NH$_4$OH Diluted in Water

| Sample | Concentration (ppm) | Surface Tension (dyn/cm) | Soluble |
|---|---|---|---|
| Example 19 FBSEE | 1000 | 36.5 | Yes |
| | 2000 | 29.3 | Yes |
| | 4000 | 22.4 | Yes |
| Example 20 FBS(EE)2 | 1000 | 34.1 | Yes |
| | 2000 | 22.4 | Yes |
| | 4000 | 22.8 | Yes |
| Example 21 FBSPE | 1000 | 20.8 | Yes |
| | 2000 | 19.4 | Yes |
| | 4000 | 18.9 | Yes |
| | 6000 | 18.3 | No |
| Example 22 FBSE(EE) | 1000 | 27.1 | Yes |
| | 2000 | 23.7 | Yes |
| | 4000 | 19.9 | Yes |
| | 6000 | 18.9 | Yes |
| | 8000 | 18.9 | Yes |
| Example 23 Pr-FBS(EE) | 1000 | 23.2 | Yes |
| | 2000 | 22.7 | No |
| | 4000 | 21.8 | No |

Examples 24-26

Solubility and Surface Tension of H-FBS(EEE) (VIII) Blends in Ammonium Hydroxide Blends of 22% H-FBS(EEE) and 3% of a neutral surfactant were made by dissolving H-FBS(EEE) with each of the following neutral surfactants—FBSEE (B), FBS(EE)2 (IV) or FBS(EEE)2 (IX). The FBS(EEE)2 used consisted of 33% FBS(EEE)2 and 66% H-FBS(EEE). Blend ratios were adjusted to account for this. Solutions were prepared in aqueous ammonium hydroxide which had been diluted in 18.2 megaohm water. The solutions were mixed for one hour and allowed to settle over night. Examples were prepared as described in Table 15.

TABLE 15

Sample Preparation of H-FBS(EEE) + Neutral Surfactants in Aqueous NH$_4$OH

| Example | 24 | 25 | 26 |
|---|---|---|---|
| Neutral | FB SEE | FBS(EE)2 | FBS(EEE)2 |
| Mass Water (g) | 6.798 | 3.407 | 3.403 |
| Mass 29% NH$_3$ (g) | 0.701 | 0.355 | 0.357 |
| Mass H-FBS(EEE) (g) | 2.198 | 1.101 | 0.782 |
| Mass Neutral (g) | 0.300 | 0.150 | 0.450 |
| Soluble | Yes | Yes | Yes |

The solutions were diluted in water for surface tension and solubility measurements. The results are summarized in Table 16.

TABLE 16

H-FBS(EEE) + Neutral Surfactants in Aqueous NH$_4$OH Diluted in Water

| Sample | Concentration (ppm) | Surface Tension (dyn/cm) | Soluble |
|---|---|---|---|
| Example 24 FBSEE | 1000 | 35.1 | Yes |
| | 2000 | 28.6 | Yes |
| | 4000 | 20.8 | Yes |
| | 6000 | 19.2 | No |
| | 8000 | 19.6 | No |
| Example 25 FBS(EE)2 | 1000 | 31.6 | Yes |
| | 2000 | 24.5 | Yes |
| | 4000 | 21.0 | Yes |
| | 6000 | 20.5 | Yes |
| | 8000 | 21.2 | Yes |
| Example 26 FBS(EEE)2 | 1000 | 31.2 | Yes |
| | 2000 | 26.0 | Yes |
| | 4000 | 22.2 | Yes |
| | 6000 | 22.1 | Yes |
| | 8000 | 23.1 | Yes |

Examples 27-31

Solubility and Surface Tension of H-FBSE (A) Blends in Ammonium Hydroxide

Blends of 22% H-FB SE and 3% of a neutral surfactant were made by dissolving H-FBSE with each of the following neutral surfactants—FBS(EE)2 (IV), FBSE(EE) (V), FBSPE (X), Me-FBS(EE) (VI) or Pr-FBS(EE) (VII). Solutions were prepared in aqueous ammonium hydroxide which had been diluted in 18.2 megaohm water. The solutions were mixed for one hour and allowed to settle over night. Examples were prepared as described in Table 17.

TABLE 17

Sample Preparation of H-FBSE + Neutral Surfactants in Aqueous NH$_4$OH

| Example | 27 | 28 | 29 | 30 | 31 |
|---|---|---|---|---|---|
| Neutral | FBS(EE)2 | FBSE(EE) | FBSPE | Me-FBS(EE) | Pr-FBS(EE) |
| Mass Water (g) | 6.65 | 6.647 | 6.649 | 6.662 | 6.661 |
| Mass 29% NH$_3$ (g) | 0.85 | 0.864 | 0.846 | 0.848 | 0.856 |
| Mass H-FBSE (g) | 2.20 | 2.201 | 2.203 | 2.19 | 2.21 |

TABLE 17-continued

Sample Preparation of H-FBSE + Neutral Surfactants in Aqueous NH₄OH

| Example | 27 | 28 | 29 | 30 | 31 |
|---|---|---|---|---|---|
| Mass Neutral (g) | 0.30 | 0.300 | 0.296 | 0.30 | 0.300 |
| Soluble | Yes | Yes | Yes | Yes | Yes |

The solutions were diluted in water for surface tension and solubility measurements. The results are summarized in Table 18.

TABLE 18

H-FBSE + Neutral Surfactants in Aqueous NH₄OH Diluted in Water

| Sample | Concentration (ppm) | Surface Tension (dyn/cm) | Soluble |
|---|---|---|---|
| Example 27 FBS(EE)2 | 2000 | 21.6 | Yes |
| | 4000 | 19.6 | Yes |
| | 6000 | 20.0 | Yes |
| | 8000 | 20.6 | Yes |
| Example 28 FBSE(EE) | 500 | 24.2 | Yes |
| | 1000 | 23.7 | Yes |
| | 2000 | 23.5 | Yes |
| | 4000 | 20.6 | Yes |
| | 6000 | 18.6 | Yes |
| | 8000 | 18.3 | Yes |
| Example 29 FBSPE | 1000 | 24.5 | Yes |
| | 2000 | 20.4 | Yes |
| | 4000 | 19.2 | Yes |
| | 5000 | 18.5 | Yes |
| | 6000 | 18.3 | Very light haze |
| Example 30 Me-FBS(EE) | 1000 | 26.1 | Yes |
| | 2000 | 17.6 | Yes |
| | 2200 | 18.1 | Yes |
| | 2500 | 17.6 | No |
| Example 31 Pr-FBS(EE) | 1000 | 23.7 | Yes |
| | 2000 | 23.6 | No |
| | 4000 | 23.5 | No |

Example 32

Solubility and Surface Tension of FBSE(EE) (V)

A 1% solution of FBSE(EE) was prepared by dissolving molten FBSE(EE) in 18.2 megaohm water. The solution was mixed for one hour and allowed to settle over night. Example 32 was prepared as described in Table 19.

TABLE 19

Sample Preparation of FBSE(EE) in Water

| Example | Mass Water (g) | Mass FBSE(EE) (g) | Soluble |
|---|---|---|---|
| 32 | 9.903 | 0.102 | Yes |

The solution was diluted in water for surface tension and solubility measurements. The results are summarized in Table 20.

TABLE 20

FBSE(EE) Diluted in Water

| Sample | Concentration (ppm) | Surface Tension (dyn/cm) | Soluble |
|---|---|---|---|
| Example 32 | 25 | 48.2 | Yes |
| | 50 | 41.1 | Yes |
| | 100 | 32.2 | Yes |
| | 250 | 27.4 | Yes |
| | 500 | 21.6 | Yes |
| | 1000 | 18.4 | Yes |

Example 33

Solubility and Surface Tension of Pr-FBS(EE) (VII)

A 1% solution of Pr-FBS(EE) was prepared by dissolving molten Pr-FBS(EE) in iso-propyl alcohol (IPA, available from Honeywell, Morristown, N.J.). The solution was mixed and allowed to settle. Example 33 was prepared as described in Table 21.

TABLE 21

Sample Preparation of Pr-FBS(EE) in IPA

| Example | Mass IPA (g) | Mass Pr-FBS(EE) (g) | Soluble |
|---|---|---|---|
| 33 | 10.890 | 0.110 | Yes |

The solution was diluted in water for surface tension and solubility measurements. The results are summarized in Table 22.

TABLE 22

Pr-FBS(EE) Diluted in Water

| Sample | Concentration (ppm) | Surface Tension (dyn/cm) | Soluble |
|---|---|---|---|
| Example 33 | 25 | 32.7 | Yes |
| | 50 | 27.1 | Yes |
| | 100 | 23.7 | Yes |
| | 125 | 23.6 | Yes |
| | 150 | 23.2 | Yes |

Example 34

Solubility and Surface Tension of FBS(EE)2 (IV)

FBS(EE)2 was diluted in water for surface tension and solubility measurements (Example 34). The results for example 34 are summarized in Table 23.

TABLE 23

FBS(EE)2 Diluted in Water

| Sample | Concentration (ppm) | Surface Tension (dyn/cm) | Soluble |
|---|---|---|---|
| Example 34 | 50 | 41.8 | Yes |
| | 100 | 35.9 | Yes |
| | 250 | 27.6 | Yes |
| | 500 | 22.6 | Yes |

Comparative Examples 1-4

Solubility and Surface Tension of H-FBSE (A) with Ammonium Hydroxide

25% solutions of H-FBSE were prepared by dissolving molten H-FB SE in aqueous ammonium hydroxide which had been diluted with 18.2 megaohm water. The solutions were mixed for one hour and allowed to settle over night. Comparative examples 1 to 4 were prepared as described in Table 24.

TABLE 24

Sample Preparation of H-FBSE in Aqueous NH$_4$OH

| Comparative Example (CE) | Mole Ratio | Mass Water (g) | Mass 29% NH$_3$ (g) | Mass H-FBSE (g) | Soluble |
|---|---|---|---|---|---|
| CE 1 | 2.0 | 6.65 | 0.85 | 2.49 | Yes |
| CE 2 | 1.5 | 6.85 | 0.63 | 2.51 | Yes |
| CE 3 | 1.0 | 7.07 | 0.45 | 2.50 | Yes |
| CE 4 | 0.5 | 7.29 | 0.22 | 2.51 | Yes |

The solutions were diluted in water for surface tension and solubility measurements. The results are summarized in Table 25.

TABLE 25

H-FBSE in Aqueous NH$_4$OH Diluted in Water

| Sample | Concentration (ppm) | Surface Tension (dyn/cm) | Soluble |
|---|---|---|---|
| CE 1 | 1000 | 60.7 | Yes |
| Mole Ratio 2.0 | 2000 | 50.2 | Yes |
|  | 4000 | 49.2 | Yes |
|  | 6000 | 42.8 | Yes |
|  | 8000 | 41.2 | Yes |
| CE 2 | 1000 | 49.5 | Yes |
| Mole Ratio 1.5 | 2000 | 45.9 | Yes |
|  | 4000 | 40.1 | Yes |
|  | 6000 | 37.4 | Yes |
|  | 8000 | 35.5 | Yes |
| CE 3 | 1000 | 41.7 | Yes |
| Mole Ratio 1.0 | 2000 | 34.5 | Yes |
|  | 4000 | 27.9 | Yes |
|  | 6000 | 23.6 | Yes |
|  | 8000 | 20.8 | Yes |
| CE 4 | 1000 | 29.9 | Yes |
| Mole Ratio 0.5 | 2000 | 22.7 | Yes |
|  | 3000 | 18.4 | No |
|  | 4000 | 17.8 | No |

Comparative Example 5

Solubility and Surface Tension of Blend of H-FB SE (A) and FBSEE (B) with Ammonium Hydroxide A 25% solution of a blend of H-FB SE and FBSEE were prepared by dissolving the molten H-FBSE and FBSEE in aqueous ammonium hydroxide which had been diluted with 18.2 megaohm water. The solution was mixed for one hour and allowed to settle over night. Comparative example 5 was prepared as described in Table 26.

TABLE 26

Sample Preparation of H-FBSE + FBSEE in Aqueous NH$_4$OH

| Comparative Example | Mass Water (g) | Mass 29% NH$_3$ (g) | Mass H-FBSE (g) | Mass FBSEE (g) | Soluble |
|---|---|---|---|---|---|
| CE 5 | 6.65 | 0.85 | 2.20 | 0.30 | Yes |

The solution was diluted in water for surface tension and solubility measurements. The results are summarized in Table 27.

TABLE 27

H-FBSE + FBSEE in Aqueous NH$_4$OH Diluted in Water

| Sample | Concentration (ppm) | Surface Tension (dyn/cm) | Soluble |
|---|---|---|---|
| CE 5 | 2000 | 31.3 | Yes |
|  | 4000 | 24.3 | Yes |
|  | 6000 | 24.5 | No |

Comparative Examples 6-7

Solubility and Surface Tension of Blend of FES(EE)2 (E) with H-FBS(EE) (III) and H-FBS(EEE) (VIII) in Aqueous Ammonium Hydroxide A 25% blend of FES(EE)2 with H-FBS(EE) was prepared by dissolving H-FBS(EE) and FES(EE)2 in aqueous ammonium hydroxide which had been diluted in 18.2 megaohm water. A similar solution was prepared using FES(EE)2 and H-FBS(EEE). The solutions were mixed for one hour and allowed to settle overnight. Comparative examples 6 and 7 were prepared as described in Table 28.

TABLE 28

Sample Preparation of FES(EE)2 with Anionic Surfactants in Aqueous NH$_4$OH

| Comparative Example | CE 6 | CE 7 |
|---|---|---|
| Anionic | H-FBS(EE) | H-FBS(EEE) |
| Mass Water (g) | 3.371 | 3.396 |
| Mass 29% NH$_3$ (g) | 0.386 | 0.349 |
| Mass Anionic (g) | 1.096 | 1.101 |
| Mass FES(EE)2 | 0.150 | 0.154 |
| Soluble | Yes | Yes |

The solutions were diluted in water for surface tension and solubility measurements. The results are summarized in Table 29.

TABLE 29

FES(EE)2 + Anionic Surfactants in Aqueous NH$_4$OH Diluted in Water

| Comparative Example | Concentration | Surface Tension | Soluble |
|---|---|---|---|
| CE 6 | 1000 | 45.2 | Yes |
| H-FBS(EE) + | 2000 | 39.5 | Yes |
| FES(EE)2 | 4000 | 33.9 | Yes |
|  | 6000 | 30.7 | Yes |
|  | 8000 | 28.2 | Yes |
| CE 7 | 1000 | 42.5 | Yes |
| H-FBS(EEE) + | 2000 | 35.6 | Yes |
| FES(EE)2 | 4000 | 29.8 | Yes |

TABLE 29-continued

FES(EE)2 + Anionic Surfactants in Aqueous NH₄OH Diluted in Water

| Comparative Example | Concentration | Surface Tension | Soluble |
|---|---|---|---|
| | 6000 | 27.8 | Yes |
| | 8000 | 26.4 | Yes |

Comparison of Water Contact Angles after Rinsing

The shift in the contact angle of water on a photoresist after exposure to a surfactant solution was measured using a DSA 100 (available from Krüss of Hamburg, Germany).

A photoresist material (EPIC 2135 193 nm photoresist available from Dow Chemical Co., Midland, Mich.) was spin coated on one side of a piece of silicon wafer—approximately 1 inch by 1 inch using a spin rate of 1500 rpm for 27 seconds. The photoresist was baked to drive off solvent by placing the wafer on a hot plate at 120° C. for 60 seconds.

The wafer coated with resist was placed in a spin coater (WS-650 MZ-23NPP/LITE from Laurell Technologies of North Wales, Pa.) with a modified chuck. While the wafer was spinning at 300 rpm, 1 mL of 2.38% TMAH (available from Alfa Aesar of Ward Hill, Mass.) was applied to the wafer over 20 seconds. This was followed by 10 mL of 18.2 megaohm water applied over 60 seconds and then 1.5 mL of surfactant solution applied over 40 seconds. The spin rate was then increased to 1500 rpm and held for 15 seconds. While still spinning at 1500 rpm, a nitrogen stream was then placed over the wafer for 15 seconds. The water contact angle was then immediately measured.

The measured static water contact angles are reported in Table 30. All the surfactant solutions in the table were diluted to 2000 ppm total surfactant in water. In all cases, there were no visible changes to the photoresist after exposure to the surfactant solution.

TABLE 30

Static Water Contact Angle on Photoresist

| Example | Sample | Water Contact Angle |
|---|---|---|
| N/A | Wafer - No Resist | 34.1 (±0.8) |
| N/A | Resist - No Rinse | 64.7 (±1.3) |
| N/A | Resist - TMAH + Water Only | 56.6 (±1.0) |
| Comparative Example 5 | H-FBSE/FBSEE | 41.0 (±0.6) |
| Example 27 | H-FBSE/FBS(EE)2 | 44.3 (±1.0) |
| Example 28 | H-FBSE/FBSE(EE) | 45.7 (±0.9) |
| Example 24 | H-FBS(EEE)/FBSEE | 43.2 (±0.6) |
| Example 25 | H-FBS(EEE)/FBS(EE)2 | 42.4 (±1.3) |
| Example 26 | H-FBS(EEE)/FBS(EEE)2 | 39.6 (±0.8) |
| Comparative Example 1 | H-FBSE, Mole Ratio 2.0 | 54.7 (±1.7) |
| Comparative Example 3 | H-FBSE, Mole Ratio 1.0 | 49.1 (±1.9) |
| Example 5 | H-FBS(EE), Mole Ratio 2.0 | 46.4 (±0.6) |
| Example 7 | H-FBS(EE), Mole Ratio 1.0 | 45.8 (±0.6) |
| Example 13 | H-FBS(EEE), Mole Ratio 2.0 | 43.9 (±1.1) |
| Example 15 | H-FBS(EEE), Mole Ratio 1.0 | 44.5 (±0.8) |

The results of these experiments demonstrate that the choice of surfactants, blending of selected anionic and neutral surfactants, and adjusting pH can affect water contact angles on developed and rinsed photoresist surface, thus providing a means to control contact angles.

Comparison of Surfactant Absorption on Photoresist

The absorption of several surfactant solutions diluted in water to a photoresist material (EPIC 2135 193 nm photoresist) was measured using a Q-Sense E4 QCM-D microbalance (available from Biolin Scientific, Västra Frölunda, SWEDEN). This instrument analyzes both the dissipation and frequency shift of a quartz crystal sensor to characterize thin films coated on the sensor. This allows the mass of material absorbed and the viscoelastic properties of the thin film to be measured. In these particular experiments, it allows measurement of the mass of surfactant absorbed onto or into the photoresist material during exposure of the resist to the surfactant solution.

A gold plated quartz crystal sensor (QSX 301, Biolin Scientific, Sweden) was single side coated with photoresist (EPIC 2135 193 nm) by spin coating. One to three droplets of the resist material were applied to a clean sensor. The sensor was then spun at 1500 rpm for 27 seconds. The resist was baked to drive off solvent by placing the sensor on a hot plate at 120° C. for 60 seconds.

The coated sensors were then tested in three stages. During all stages, dissipation and frequency shift were monitored on multiple bands. In the first phase, 18 megaohm water was run over the sensor (at 150 μL/min) for five minutes to establish a baseline. No frequency shift or dissipation was observed during this stage. Once the baseline was established, the second stage was started by switching the flow to the surfactant solution (at 150 μL/min). This flow was continued until the frequency shift and dissipation stabilized (generally 15 minutes). Reported values for frequency shift were measured at this time. In the third stage, the flow was switched back to pure 18 megaohm water (at 150 μL/min). The shift in frequency and dissipation were again monitored for 10 minutes to determine if surfactant absorption was reversible.

The steady state frequency shifts due to absorption of several surfactants from solution at 2000 ppm in water during surfactant solution flow are recorded in Table 31 below.

TABLE 31

Absorption Values by QCM-D on Photoresist

| Set/Example | Sample | Absorption (ΔV) |
|---|---|---|
| Comparative Example 5 | H-FBSE/FBSEE | 4.0 |
| Example 27 | H-FBSE/FBS(EE)2 | 8.2 |
| Example 28 | H-FBSE/FBSE(EE) | 9.9 |
| Example 24 | H-FBS(EEE)/FBSEE | 6.7 |
| Example 25 | H-FBS(EEE)/FBS(EE)2 | 7.9 |
| Example 26 | H-FBS(EEE)/FBS(EEE)2 | 7.5 |
| Comparative Example 1 | H-FBSE, Mole Ratio 2.0 | 2.0 |
| Comparative Example 3 | H-FBSE, Mole Ratio 1.0 | 3.8 |
| Example 5 | H-FBS(EE), Mole Ratio 2.0 | 3.1 |
| Example 7 | H-FBS(EE), Mole Ratio 1.0 | 5.7 |
| Example 13 | H-FBS(EEE), Mole Ratio 2.0 | 4.0 |
| Example 15 | H-FBS(EEE), Mole Ratio 1.0 | 6.7 |

The results of these experiments demonstrate that the choice of surfactants, blending of selected anionic and neutral surfactants, and adjusting pH can affect the level (or mass) of surfactant absorbed onto or into the photoresist from aqueous rinse solutions, thus providing a means to control surfactant absorption by the photoresist. This in turn can provide control of contact angles on the resist surface as well as various lithography performance attributes such as defectivity (numbers of watermarks and particle defects), line melting, line width roughness, line edge roughness and process windows.

Comparisons of Surface Tension Performance and Solubility:

Comparison of H-FBSE, H-FBSP, H-FBS(EE) and H-FBS(EEE) in Aqueous Ammonium Hydroxide Surface tension and solubility results in water from examples 1, 5, 13 and comparative example 1 are summarized in Table 32 below for mole ratio of 2.0.

TABLE 32

Surface Tension (dyn/cm)/Solubility of Anionic Surfactants in Aqueous Ammonia, MR2.0

| Concentration (ppm) | H-FBSP (Ex 1) | H-FBS(EE) (Ex 5) | H-FBS(EEE) (Ex 13) | H-FBSE (CE 1) |
|---|---|---|---|---|
| 1000 |  | 47.9/Yes | 39.9/Yes | 60.7/Yes |
| 2000 | 51.6/Yes | 42.1/Yes | 35.2/Yes | 50.2/Yes |
| 4000 | 46.2/Yes | 35.5/Yes | 31.4/Yes | 49.2/Yes |
| 6000 | 42.8/Yes | 32.9/Yes | 29.2/Yes | 42.8/Yes |
| 8000 | 40.5/Yes | 30.4/Yes | 27.6/Yes | 41.2/Yes |

All solutions tested were soluble. The H-FBS(EE) and H-FBS(EEE) provide lower surface tension in water than the H-FB SE at the same concentrations with the H-FBS(EEE) providing the lowest surface tension in water of all the materials tested. H-FBSE and H-FB SP provide roughly equivalent surface tensions.

Surface tension and solubility results in water from examples 2, 6, 14 and comparative example 2 are summarized in Table 33 below for mole ratio of 1.5.

TABLE 33

Surface Tension (dyn/cm)/Solubility of Anionic Surfactants in Aqueous Ammonia, MR1.5

| Concentration (ppm) | H-FBSP (Ex 2) | H-FBS(EE) (Ex 6) | H-FBS(EEE) (Ex 14) | H-FBSE (CE 2) |
|---|---|---|---|---|
| 1000 |  | 46.6/Yes | 38.7/Yes | 49.5/Yes |
| 2000 | 47.9/Yes | 41.1/Yes | 33.3/Yes | 45.9/Yes |
| 4000 | 41.6/Yes | 34.5/Yes | 29.4/Yes | 40.1/Yes |
| 6000 | 37.9/Yes | 31.4/Yes | 26.6/Yes | 37.4/Yes |
| 8000 | 35.6/Yes | 28.8/Yes | 25.4/Yes | 35.5/Yes |

The relative performance of these surfactants for the mole ratio of 1.5 follows the same trend as the mole ratio of 2.0, above.

Surface tension and solubility results in water from examples 3, 7, 15 and comparative example 3 are summarized in Table 34 below for mole ratio of 1.0.

TABLE 34

Surface Tension (dyn/cm)/Solubility of Anionic Surfactants in Aqueous Ammonia, MR1.0

| Concentration (ppm) | H-FBSP (Ex 3) | H-FBS(EE) (Ex 7) | H-FBS(EEE) (Ex 15) | H-FBSE (CE 3) |
|---|---|---|---|---|
| 1000 | Concentrate is not soluble | 36.8/Yes | 34.0/Yes | 41.7/Yes |
| 2000 |  | 30.3/Yes | 28.4/Yes | 34.5/Yes |
| 4000 |  | 24.1/Yes | 24.5/Yes | 27.9/Yes |
| 6000 |  | 21.1/Yes | 22.5/Yes | 23.6/Yes |
| 8000 |  | 20.1/Yes | 20.8/Yes | 20.8/Yes |

All the tested dilutions in water are soluble. H-FBS(EE) and H-FBS(EEE) provide lower surface tensions than H-FBSE at low surfactant concentrations in water. At higher surfactant concentrations, the surface tension results are equivalent for all three.

Surface tension and solubility results in water from examples 4, 8, 16 and comparative example 4 are summarized in Table 35 below for mole ratio of 0.5.

TABLE 35

Surface Tension (dyn/cm)/Solubility of Anionic Surfactants in Aqueous Ammonia, MR0.5

| Concentration (ppm) | H-FBSP (Ex 4) | H-FBS(EE) (Ex 8) | H-FBS(EEE) (Ex 16) | H-FBSE (CE 4) |
|---|---|---|---|---|
| 1000 | Concentrate is not soluble | 29.4/Yes | 26.5/Yes | 29.9/Yes |
| 2000 |  | 24.7/No | 23.2/Yes | 22.7/Yes |
| 4000 |  | 21.0/No | 21.6/No | 17.8/No |

All of the anionic surfactants tested have limited solubility under these conditions. In the soluble range, the surface tensions are similar for all three materials.

Comparison of H-FB SE, H-FBS(EE) and H-FBS(EEE) in Aqueous TMAH

Surface tension and solubility results in water from Example 9 (H-FBS(EE)) and similar data collected for H-FBS(EEE) and H-FBSE under identical conditions are summarized in Table 36 below for a mole ratio of 2.0.

TABLE 36

Surface Tension (dyn/cm)/Solubility of Anionic Surfactants in Aqueous TMAH, MR2.0

| Concentration (ppm) | H-FBS(EE) (Ex 9) | H-FBS(EEE) (Ex 35) | H-FBSE (CE 8) |
|---|---|---|---|
| 1000 | 46.4/Yes | 47.3/Yes | 62.3/Yes |
| 2000 | 41.4/Yes | 42.6/Yes | 59.0/Yes |
| 4000 | 35.8/Yes | 38.6/Yes | 55.3/Yes |
| 6000 | 32.4/Yes | 35.0/Yes | 51.3/Yes |
| 8000 | 30.3/Yes | 32.8/Yes | 49.3/Yes |

All solutions tested were completely soluble. The H-FBS(EE) and H-FBS(EEE) surfactants provide significantly lower surface tension in water than H-FBSE at the same concentrations.

Surface tension and solubility results in water from Example 10 (H-FBS(EE)) and similar data collected for H-FBS(EEE) and H-FBSE under identical conditions are summarized in Table 37, below, for a mole ratio of 1.5.

TABLE 37

Surface Tension (dyn/cm)/Solubility of Anionic Surfactants in Aqueous TMAH, MR1.5

| Concentration (ppm) | H-FBS(EE) (Ex 10) | H-FBS(EEE) (Ex 36) | H-FBSE (CE 9) |
|---|---|---|---|
| 1000 | 46.5/Yes | 47.4/Yes | 60.8/Yes |
| 2000 | 41.0/Yes | 42.9/Yes | 61.3/Yes |
| 4000 | 35.7/Yes | 37.9/Yes | 55.0/Yes |
| 6000 | 32.5/Yes | 35.7/Yes | 52.7/Yes |
| 8000 | 30.0/Yes | 33.5/Yes | 49.9/Yes |

Relative surface tension and solubility results are similar to the MR 2.0 results, described above.

Surface tension and solubility results in water from Example 11 (H-FBS(EE)) and similar data collected for H-FBS(EEE) and H-FBSE under identical conditions are summarized in Table 38 below for a mole ratio of 1.0.

TABLE 38

Surface Tension (dyn/cm)/Solubility of Anionic Surfactants in Aqueous TMAH, MR1.0

| Concentration (ppm) | H-FBS(EE) (Ex 11) | H-FBS(EEE) (Ex 37) | H-FBSE (CE 10) |
|---|---|---|---|
| 1000 | 45.4/Yes | 44.2/Yes | 53.3/Yes |
| 2000 | 40.6/Yes | 42.2/Yes | 47.1/Yes |
| 4000 | 34.7/Yes | 36.6/Yes | 46.6/Yes |
| 6000 | 32.4/Yes | 33.2/Yes | 42.9/Yes |
| 8000 | 29.5/Yes | 30.3/Yes | 42.5/Yes |

Both H-FBS(EE) and H-FBS(EEE) provide significantly lower surface tensions than H-FBSE at equivalent concentrations when tested at this mole ratio (MR1.0), similar to results at higher MR.

Surface tension and solubility results in water from Example 12 (H-FBS(EE)) and similar data collected for H-FBS(EEE) and H-FBSE under identical conditions are summarized in Table 39, below, for a mole ratio of 0.5.

TABLE 39

Surface Tension (dyn/cm)/Solubility of Anionic Surfactants in Aqueous TMAH, MR0.5

| Concentration (ppm) | H-FBS(EE) (Ex 12) | H-FBS(EEE) (Ex 38) | H-FBSE (CE 11) |
|---|---|---|---|
| 1000 | 28.2/Yes | 26.7/Yes | 31.1/Yes |
| 2000 | 23.4/No | 22.8/Yes | 24.1/Yes |
| 4000 | 20.3/No | 20.8/No | 16.7/No |

All of the anionic surfactants tested have limited solubility under these conditions. In the soluble range, the surface tensions of H-FBS(EE) and H-FBS(EEE) are slightly lower than those provided by H-FB SE.

Comparison of FBSEE, FBS(EE)2 and FBSE(EE) Blended with H-FBSE in Aqueous Ammonium Hydroxide Surface tension and solubility results in water from examples 27, 28 and comparative example 5 are summarized in Table 40. For the data presented below, the concentrates were prepared at 22 wt % H-FB SE and 3 wt % of either FBSEE, FBS(EE)2, or FBSE(EE) in aqueous ammonium hydroxide, and then diluted with water to the stated concentration.

TABLE 40

Surface Tension (dyn/cm)/Solubility of Neutral Surfactant Blends with H-FBSE

| Concentration (ppm) | FBSE(EE) (Ex 28) | FBS(EE)2 (Ex 27) | FBSEE (CE 5) |
|---|---|---|---|
| 2000 | 23.5/Yes | 21.6/Yes | 31.3/Yes |
| 4000 | 20.6/Yes | 19.6/Yes | 24.3/Yes |
| 6000 | 18.6/Yes | 20.0/Yes | 24.5/No |
| 8000 | 18.3/Yes | 20.6/Yes | |

Blends of FBSE(EE) and FBS(EE)2 with H-FB SE provide lower surface tension and better solubility than the comparative H-FBSE/FBSEE blend.

Comparison of Blends of FB SEE, FBS(EE)2 and FBS(EEE)2 with H-FBS(EEE) in Aqueous Ammonium Hydroxide Vs. FBSEE/H-FBSE Blend Surface tension and solubility results in water for surfactants described Examples 24-26 are summarized in Table 41 below. The concentrates for these examples were prepared at 22 wt % H-FBS(EEE) blended with 3 wt % of either FBSEE, FBS(EE)2, or FBS(EEE)2 in aqueous ammonium hydroxide, and then diluted with water to the stated concentration. Comparative results for the blend of H-FBSE/FBSEE prepared and tested under identical conditions (Comparative Example 5) are included for comparison.

TABLE 41

Surface Tension (dyn/cm)/Solubility of Neutral Surfactant Blends with H-FBS(EEE)

| Concentration (ppm) | FBS(EE)2 (Ex 25) | FBS(EEE)2 (Ex 26) | FBSEE (Ex 24) | FBSEE/FBSEE (CE 5) |
|---|---|---|---|---|
| 1000 | 31.6/Yes | 31.2/Yes | 35.1/Yes | — |
| 2000 | 24.5/Yes | 26.0/Yes | 28.6/Yes | 31.3/Yes |
| 4000 | 21.0/Yes | 22.2/Yes | 20.8/Yes | 24.3/Yes |
| 6000 | 20.5/Yes | 22.1/Yes | 19.2/No | 24.5/No |
| 8000 | 21.2/Yes | 23.1/Yes | 19.6/No | — |

Measured surface tensions are slightly lower for blends of FBS(EE)2 and FBS(EEE)2 with H-FBS(EEE) than the H-FBS(EEE)/FBSEE blend at low concentrations (1000-2000 ppm). In addition, the H-FBS(EEE) blends with FBS(EE)2 and FBS(EEE)2 provide higher solubility in water than the H-FBS(EEE)/FBSEE blend or the comparative H-FBSE/FBSEE blend. All of the surfactant blends of the present invention tested here, comprising at least one surfactant component having at least one oligomeric ethylene oxide group, provide lower surface tensions than the comparative blend of H-FBSE/FB SEE when prepared and tested under identical conditions in aqueous ammonium hydroxide.

Comparison of Blends of FES(EE)2 and FBS(EE)2 with H-FBS(EEE) in Aqueous Ammonium Hydroxide Surface tension and solubility results in water for the surfactants described in example 25), Comparative 6 and Example 13 are summarized in Table 42 below. The concentrates for the first two were prepared at 22% H-FBS(EE) and 3% of either FES(EE)2 or FBS(EE)2 in aqueous ammonium hydroxide, and then diluted in water to the state concentration. The concentrate for the latter example was prepared by dissolving 25% H-FBS(EEE) in aqueous ammonium hydroxide, and then diluted in water to the stated concentrations.

TABLE 42

Surface Tension (dyn/cm)/Solubility of Neutral Surfactant Blends with H-FBS(EEE)

| Concentration (ppm) | H-FBS(EEE)/ FBS(EE)2 (Ex 25) | H-FBS(EEE)/ FES(EE)2 (CE 6) | H-FBS(EEE) (Ex 3) |
|---|---|---|---|
| 1000 | 31.6/Yes | 42.5/Yes | 39.9/Yes |
| 2000 | 24.5/Yes | 35.6/Yes | 35.2/Yes |
| 4000 | 21.0/Yes | 29.8/Yes | 31.4/Yes |
| 6000 | 20.5/Yes | 27.8/Yes | 29.2/Yes |
| 8000 | 21.2/Yes | 26.4/Yes | 27.6/Yes |

Surface tension results are significantly lower for H-FBS(EEE)/FBS(EE)2 compared to H-FBS(EEE)/FES(EE)2 at equivalent concentrations. The surface tension results for H-FBS(EEE)/FES(EE)2 are essentially the same as H-FBS(EEE) alone at equivalent total surfactant concentrations. The addition of the FBS(EE)2 significantly improves the surface tension performance, but the addition of FES(EE)2 has essentially no affect on the surface tension of the solution. This indicates that the specific choice of neutral surfactant additive is critical to the surface tension performance of such surfactant blends.

Solubility Test Results for Individual Neutral Surfactants in Water

Various neutral fluorinated surfactants were tested to determine their solubility in pure deionized water. Solubility test results are summarized in Table 43. The solubility data indicate that neutral surfactants of the present invention comprising oligomeric ethylene oxide groups (identified by Roman numerals) generally provide superior solubility in water compared to similar art known neutral fluorinated surfactants (identified by letters of alphabet) lacking oligomeric ethylene oxide groups.

TABLE 43

Solubility for Neutral Fluorinated Surfactants in Water at 22° C.

| Structure # | Compound | Acronym | % Soluble in water at 22 Deg C.* |
|---|---|---|---|
| B (Comparative) | [structure] | FBSEE | 0.0592 |
| V | [structure] | FBSE(EE) | 100 (miscible)^ |
| IV | [structure] | FBS(EE)2 | 0.101 |
| C (Comparative) | [structure] | Me-FBSE** | 0.118 |
| VI | [structure] | Me-FBSEE | 0.232 |

*Neutral fluorinated surfactant samples saturated in water were either filtered or phase split and the homogeneous aqueous solutions were submitted for analysis via capillary gas chromatography to determine their solubility in Water at 22° C. The analyses were performed using an Agilent 6890N gas chromatograph with a Flame Ionization Detector (FID), an Agilent 7683A automatic sampler, and an HP-1, 30 m, 0.25 mm ID, 1 um df capillary column. Standards were prepared between 0.1% (W/V) and 0.0001% (W/V) in Tetrahydrofuran (THF) stabilized with 0.025% (W/V) BHT [used as an internal standard] or acetonitrile. The samples were dissolved and diluted to 10% (W/V) in stabilized THF or acetonitrile.
^Surfactant Sample was found to dissolve at both 10% and 90% solids in water—completely miscible with water.
**Me-FBSE was prepared as described in U.S. Pat. No. 3,734,962

Other embodiments of the invention are within the scope of the appended claims.

The invention claimed is:

1. A fluorinated sulfonamide surfactant composition comprising:
    a neutral surfactant according to the formula:
    $R_fSO_2N[CH_2CH(CH_3)OH]_2$;
    $R_fSO_2N[CH_2CH(CH_3)OH][(CH_2CH_2O)_nH]$, where n is an integer from 1-6; or
    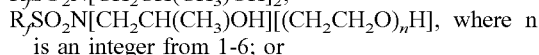
    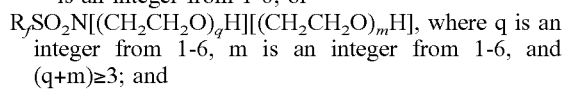
    $R_fSO_2N[(CH_2CH_2O)_qH][(CH_2CH_2O)_mH]$, where q is an integer from 1-6, m is an integer from 1-6, and $(q+m) \geq 3$; and
    a solvent comprising water;
    wherein $R_f$ is a fluoroalkyl group having 3 to 8 carbon atoms.

2. A composition according to claim 1, wherein m is an integer $\leq 3$.

3. A composition according to claim 1, wherein m is 3.

4. A composition according to claim 1, wherein the fluoroalkyl group is saturated.

5. A composition according to claim 1, wherein the fluoroalkyl group is straight chain.

6. A composition according to claim 1, wherein the fluoroalkyl group is a perfluoroalkyl group.

7. A composition according to claim 1, wherein the fluoroalkyl group has 4 to 6 carbon atoms.

8. A composition according to claim 1, wherein the fluoroalkyl group is a saturated perfluoroalkyl group having 4 to 6 carbon atoms.

9. A composition according to claim 1, wherein the fluoroalkyl group is a saturated perfluoroalkyl group having 4 carbon atoms.

10. A composition according to claim 1, wherein the neutral surfactant includes at least one oligomeric ethylene oxide group bonded to the sulfonamide nitrogen atom, wherein the oligomeric ethylene oxide group has 2-6 ethylene oxide repeat units.

11. A method of treating a surface of a photoresist material, the method comprising:

exposing the photoresist material to a composition according to claim 1.

* * * * *